(12) United States Patent
Kagabu et al.

(10) Patent No.: US 8,309,733 B2
(45) Date of Patent: Nov. 13, 2012

(54) IMINO DERIVATIVES, METHODS FOR PRODUCING THE SAME AND INSECTICIDES CONTAINING THE SAME

(75) Inventors: Shinzo Kagabu, Gifu (JP); Masaru Mori, Iwaki (JP); Satoru Kumazawa, Iwaki (JP)

(73) Assignees: Meji Seika Pharma Co., Ltd., Tokyo-To (JP); Gifu University, Gifu (JP)

( * ) Notice: Subject to any disclaimer, the term of this patent is extended or adjusted under 35 U.S.C. 154(b) by 0 days.

(21) Appl. No.: 13/001,843

(22) PCT Filed: Jul. 1, 2009

(86) PCT No.: PCT/JP2009/062032
§ 371 (c)(1),
(2), (4) Date: Mar. 28, 2011

(87) PCT Pub. No.: WO2010/001922
PCT Pub. Date: Jan. 7, 2010

(65) Prior Publication Data
US 2011/0172433 A1     Jul. 14, 2011

(30) Foreign Application Priority Data
Jul. 1, 2008  (JP) ................. 2008-172259

(51) Int. Cl.
*C07D 417/04*    (2006.01)
(52) U.S. Cl. .................................... 546/270.4
(58) Field of Classification Search ............... None
See application file for complete search history.

(56) References Cited

U.S. PATENT DOCUMENTS

| | | | |
|---|---|---|---|
| 4,616,025 A | 10/1986 | Ezer et al. | |
| 5,744,475 A | 4/1998 | Yano et al. | |
| 6,159,969 A | 12/2000 | Yano et al. | |
| 6,294,535 B1 | 9/2001 | Yano et al. | |
| 2007/0010532 A1 | 1/2007 | Araki et al. | |

FOREIGN PATENT DOCUMENTS

| | | |
|---|---|---|
| EP | 0 268 915 A2 | 1/1988 |
| EP | 0 763 529 A1 | 3/1997 |
| EP | 1 176 141 A1 | 1/2002 |
| JP | 57-193475 A | 11/1982 |
| JP | 59-196877 A | 11/1984 |
| JP | 63-150275 A | 6/1988 |
| JP | 63-253084 A | 10/1988 |
| JP | 2007-506674 A | 3/2007 |
| WO | 96/30346 A1 | 10/1996 |
| WO | 00/53582 A1 | 9/2000 |
| WO | 2005/005412 A1 | 1/2005 |

OTHER PUBLICATIONS

I. Lantos et al., "Antiinflammatory Activity of 5,6-Diaryl-2,3-dihydroimidazo(2,1-b)thiazoles. Isomeric 4-Pyridyl and 4-Substituded Phenyl Derivatives", Journal of Medicinal Chemistry (1984) vol. 27, No. 1 "American Chemical Society", 1984, pp. 72-75.

Eiki Watanabe et al., "Evaluation and Validation of a Commercially Available Enzyme-Linked Immunosorbent Assay for the Neonicotinoid Insecticide Imidacloprid in Agricultural Samples", Journal of Agricultural and Food Chemistry (2004) vol. 52, No. 10 "American Chemical Society", Apr. 14, 2004, pp. 2756-2762.

Ikuya Ohno et al., "Molecular Features of Neonicotinoid Pharmacophore Variants Interacting with the Insect Nicotinic Receptor", Chemical Research Toxicol (2009) vol. 22, No. 3 "Amercian Chemical Society", Jan. 29, 2009, pp. 476-482.

EPO Office Action Mailed Sep. 11, 2011 in EP 09773500.5-1211/2305658.

Journal of Medicinal Chemistry vol. 42 No. 12 1999, pp. 2227-2234.

Kevin A. Ford et al: "Chloropyridinal Neonicotinoid Insecticides: Diverse Molecular Substituents Contribute to Facile Metabolism in Mice" Chemical Research in Toxicology, vol. 19 No. 7 Jul. 1, 2006 pp. 944-951 XP55003365 ISSN: 0893-228X DOI: 10.1021/tx0600696.

*Primary Examiner* — Janet Andres
*Assistant Examiner* — Timothy R Rozof
(74) *Attorney, Agent, or Firm* — Greenblum & Bernstein P.L.C.

(57) ABSTRACT

[Technical Problem]
To provide a novel imino derivative capable of being an insecticide compound having excellent characteristics such as sustained effects and broad spectrum.
[Solution to Problem]
To provide an imino derivative represented by Formula (1).

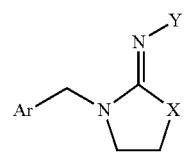

Formula (1)

wherein "Ar" denotes a heterocyclic group which may have a substituent on the ring; "X" denotes a sulfur atom or $CH_2$, NR; "R" denotes a hydrogen atom or an alkyl group; "Y" is selected from $COR_1$ or $CONR_3R_4$, $CONHCOR_5$, $CO_2R_9$; and each of "$R_1$", "$R_3$", "$R_4$", "$R_5$", and "$R_9$" denotes a hydrogen atom or a certain substituent.

4 Claims, 1 Drawing Sheet

IMINO DERIVATIVES, METHODS FOR PRODUCING THE SAME AND INSECTICIDES CONTAINING THE SAME

TECHNICAL FIELD

The present invention relates to a novel imino derivative, a method for producing the same and a use thereof. More specifically, the invention relates to a novel imino derivative, a method for producing the derivative, and an insecticide containing the derivative as an active ingredient.

BACKGROUND ART

An insecticide employed in the field of agriculture has conventionally been required to have a diversity of the characteristics. The characteristics required for an insecticide may for example be sustained effects and broad spectrum, safety when handling, easiness in using in combination with other drugs or formulation auxiliaries. Being less expensive is also required as a matter of course.

In conjunction with the invention, a synthesis of a carbonyliminothiazolidine as a conventional insecticide compound having an imino structure was reported (see Patent Literature 1). Also in Patent Literature 2, an insecticide compound having a carbonyliminoimidazolidine structure was reported (see Patent Literature 2).

CITATION LIST

Patent Literature

[PTL 1] Japanese Unexamined Patent Application Publication No. 63-150275
[PTL 2] Japanese Translation of PCT No. 2007-506674

SUMMARY OF INVENTION

Technical Problem

An insecticide employed in the field of the agriculture suffers from a problem which is the appearance of a pest which has acquired a resistance against a particular drug when such a drug has been employed for a prolonged period.

In order to prevent the appearance of such a drug-resistance pest, and also to combat against such a drug-resistance pest which has already appeared, a novel insecticide having various characteristics described above are still needed to be developed in these days.

While the synthesis of a 2-trifluoromethylcarbonyl-iminothiazolidine disclosed in Patent Literature 1 and a 3-pyridylcarbonyliminoimidazolidine disclosed in Patent Literature 2 described above as insecticide compounds having imino structures was reported, no other hopeful insecticide compounds have been found.

Accordingly, a primary objective of the present invention is to provide a novel imino derivative capable of being an insecticide compound excellent in such characteristics as sustained effects and broad spectrum.

Solution to Problem

In order to solve the problems described above, the invention provides an imino derivative represented by Formula (1):

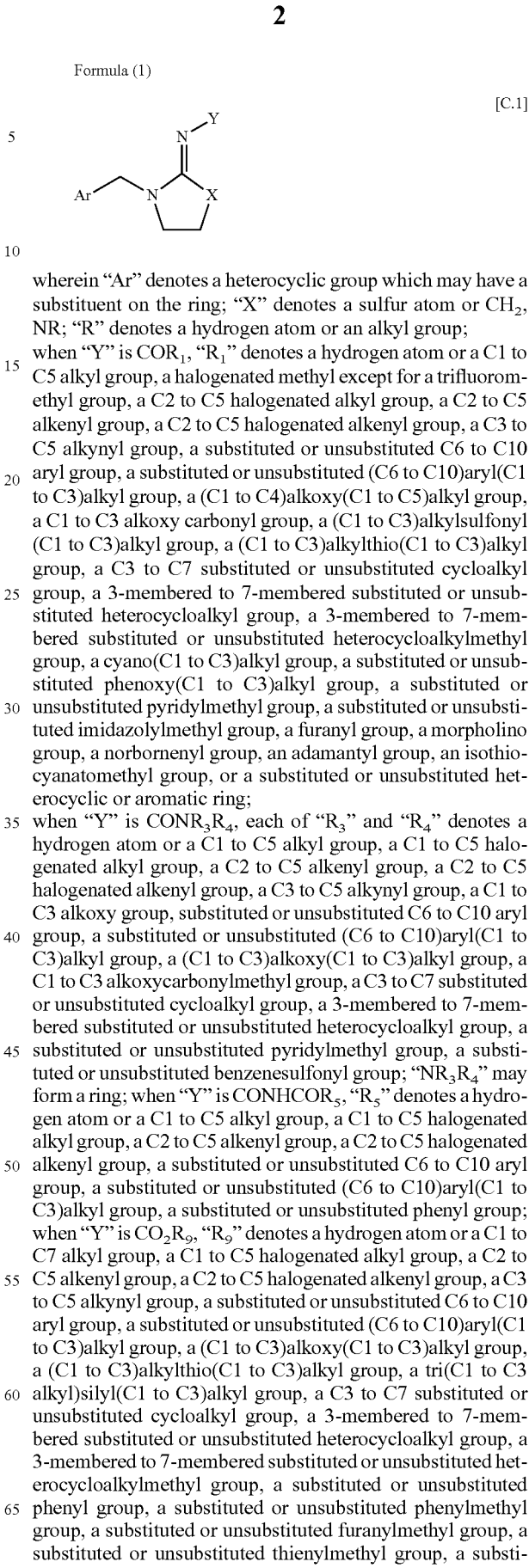

Formula (1)

[C.1]

wherein "Ar" denotes a heterocyclic group which may have a substituent on the ring; "X" denotes a sulfur atom or $CH_2$, NR; "R" denotes a hydrogen atom or an alkyl group;

when "Y" is $COR_1$, "$R_1$" denotes a hydrogen atom or a C1 to C5 alkyl group, a halogenated methyl except for a trifluoromethyl group, a C2 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C4)alkoxy(C1 to C5)alkyl group, a C1 to C3 alkoxy carbonyl group, a (C1 to C3)alkylsulfonyl (C1 to C3)alkyl group, a (C1 to C3)alkylthio(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a cyano(C1 to C3)alkyl group, a substituted or unsubstituted phenoxy(C1 to C3)alkyl group, a substituted or unsubstituted pyridylmethyl group, a substituted or unsubstituted imidazolylmethyl group, a furanyl group, a morpholino group, a norbornenyl group, an adamantyl group, an isothiocyanatomethyl group, or a substituted or unsubstituted heterocyclic or aromatic ring;

when "Y" is $CONR_3R_4$, each of "$R_3$" and "$R_4$" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a C1 to C3 alkoxy group, substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group; "$NR_3R_4$" may form a ring; when "Y" is $CONHCOR_5$, "$R_5$" denotes a hydrogen atom or a C1 to C5 alkyl group, a C1 to C5 halogenated alkyl group, a C2 to C5 alkenyl group, a C2 to C5 halogenated alkenyl group, a substituted or unsubstituted C6 to C10 aryl group, a substituted or unsubstituted (C6 to C10)aryl(C1 to C3)alkyl group, a substituted or unsubstituted phenyl group;

when "Y" is $CO_2R_9$, "$R_9$" denotes a hydrogen atom or a C1 to C7 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a (C1 to C3)alkylthio(C1 to C3)alkyl group, a tri(C1 to C3 alkyl)silyl(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a substituted or unsubstituted phenyl group, a substituted or unsubstituted phenylmethyl group, a substituted or unsubstituted furanylmethyl group, a substituted or unsubstituted thienylmethyl group, a substituted or unsubstituted pyridylmethyl group, a succinimide group, a 18-crown-6-methyl group; and the abovementioned carbon chains may be substituted with halogen.

This imino derivative has an excellent insecticidal activity against a broad range of agricultural pests and household pests.

The invention also provides a method for producing the imino derivative described above.

The first step of this production method is a step for producing a compound represented by Formula (4) by reacting a compound represented by Formula (2) with a compound (3) represented by Formula (3);

Formula (2)

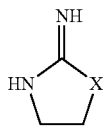
[C.2]

wherein "X" denotes a sulfur atom or $CH_2$, NR; and "R" denotes a hydrogen atom or an alkyl group.

ArCH$_2$Z     Formula (3)

wherein "Ar" denotes a heterocyclic group which may have a substituent on the ring; and "Z" denotes Cl or Br, I, $OSO_2CH_3$, $OSO_2C_6H_5$, $OSO_2C_6H_4CH_3$;

Formula (4)

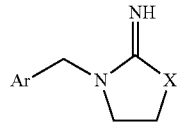
[C.4]

wherein "Ar" denotes a heterocyclic group which may have a substituent on the ring; "X" denotes a sulfur atom or $CH_2$, NR; and "R" denotes a hydrogen atom or an alkyl group.

Then, the second step of this production method is a step (I) for producing a compound (1), which is an imino derivative represented by Formula (1) shown above wherein "Y" is defined similarly to "ACO", by reacting one compound selected from the group consisting of compounds represented by Formula (5), anhydrides represented by Formula (6) and carboxylic acids represented by Formula (7) with a compound represented by Formula (4) shown above;

[C.5]

ACO—B     Formula (5)

[C.6]

ACOOCOA     Formula (6)

[C.7]

ACOOH     Formula (7)

wherein "B" denotes a halogen atom of Cl or Br, I, an OCOA group (a group formed by allowing each of an oxygen atom and a group A to form a single bond with a carbonyl group (CO)) or a hydroxyl group; when "ACO" is $COR_1$, "$R_1$" denotes a hydrogen atom or a C1 to C5 alkyl group, a halogenated methyl except for a trifluoromethyl group, a C2 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C4)alkoxy(C1 to C5)alkyl group, a C1 to C3 alkoxy carbonyl group, a (C1 to C3)alkylsulfonyl(C1 to C3)alkyl group, a (C1 to C3)alkylthio(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a cyano(C1 to C3)alkyl group, a substituted or unsubstituted phenoxy(C1 to C3)alkyl group, a substituted or unsubstituted pyridylmethyl group, a substituted or unsubstituted imidazolylmethyl group, a furanyl group, a morpholino group, a norbornenyl group, an adamantyl group, an isothiocyanatomethyl group, or a substituted or unsubstituted heterocyclic or aromatic ring;

when "ACO" is $CONR_3R_4$, each of "$R_3$" and "$R_4$" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a C1 to C3 alkoxy group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group; "$NR_3R_4$" may form a ring; and when "ACO" is $CO_2R_9$, "$R_9$" denotes a hydrogen atom or a C1 to C7 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a (C1 to C3)alkylthio(C1 to C3)alkyl group, a tri(C1 to C3 alkyl)silyl(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a substituted or unsubstituted phenyl group, a substituted or unsubstituted phenylmethyl group, a substituted or unsubstituted furanylmethyl group, a substituted or unsubstituted thienylmethyl group, a substituted or unsubstituted pyridylmethyl group, a succinimide group, a 18-crown-6-methyl group.

The second step of this production method may be Step (II) for producing an imino derivative represented by Formula (9) by reacting an isocyanate compound represented by Formula (8) with a compound represented by Formula (4) shown above;

[C.8]

D-N=C=O     Formula (8)

wherein "D" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group, $COR_5$; and "$R_5$" denotes a hydrogen atom or a C1 to C5 alkyl group, a C1 to C5 halogenated alkyl group, a C2 to C5 alkenyl group, a C2 to C5 halogenated alkenyl group, a substituted or unsubstituted C6 to C10 aryl group, a substituted or unsubstituted (C6 to C10)aryl(C1 to C3)alkyl group, a substituted or unsubstituted phenyl group.

Formula (9)

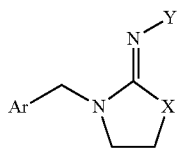

[C.9]

wherein "Ar" denotes a heterocyclic group which may have a substituent on the ring; "X" denotes a sulfur atom or $CH_2$, NR; "R" denotes a hydrogen atom or an alkyl group; "Y" denotes "CONHD", "D" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group, or $COR_5$; and "$R_5$" denotes a hydrogen atom or a C1 to C5 alkyl group, a C1 to C5 halogenated alkyl group, a C2 to C5 alkenyl group, a C2 to C5 halogenated alkenyl group, a substituted or unsubstituted C6 to C10 aryl group, a substituted or unsubstituted (C6 to C10)aryl(C1 to C3)alkyl group, a substituted or unsubstituted phenyl group.

The second step of this production method may further be Step (III) for producing an imino derivative represented by Formula (11) by reacting a formate represented by Formula (10) with a compound represented by Formula (4) shown above;

[C.10]

$HCO_2Et$      Formula (10)

Formula (11)

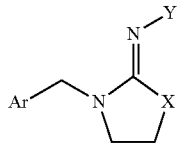

[C.11]

wherein "Ar" denotes a heterocyclic group which may have a substituent on the ring; "X" denotes a sulfur atom or $CH_2$, NR; "R" denotes a hydrogen atom or an alkyl group; and "Y" denotes CHO.

The invention further provides an insecticide containing as an active ingredient the imino derivative described above.

Advantageous Effect of the Invention

According to the invention, a novel imino derivative capable of being an insecticide compound having excellent characteristics such as sustained effects and broad spectrum is provided.

DESCRIPTION OF EMBODIMENTS

Figure 1:
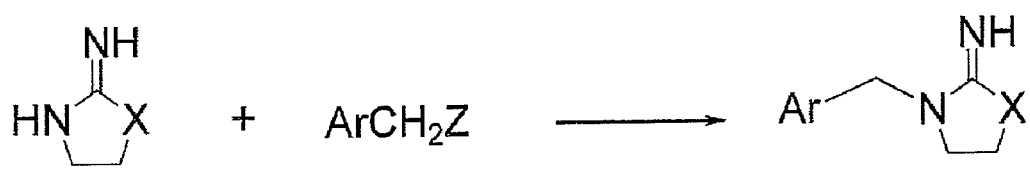
FIG. 1 shows a reaction scheme of the first step of the method for producing a novel imino derivative according to the invention.

Preferred embodiments for carrying out the invention are described below with referring to the figures. The embodiments described below are only examples of representative embodiments of the invention and do not serve to allow the scope of the invention to be interpreted narrowly.

(A) Novel Imino Derivatives

A novel imino derivative according to the invention is represented by Formula (1). Hereinafter, this imino derivative is discussed in detail.

Formula (1)

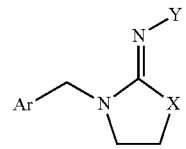

[C.12]

In Formula (1), "Ar" denotes a heterocyclic ring which may have a substituent on the ring. Typical examples of the 5-membered or 6-membered heterocyclic ring include pyridine, thiazole, tetrahydrofuran, furan, and thiazole. Those especially preferred are a 3-pyridyl group, a 5-thiazolyl group, a 3-tetrahydrofuryl group.

The substituent on the heterocyclic ring is not limited particularly and may for example be a halogen atom (any of fluorine, chlorine, bromine and iodine), a C1 to C4 alkyl group, a C1 to C4 halogenated alkyl group, a C1 to C4 alkoxy group, a di(C1 to C4 alkyl)amino group, and a nitro group. Preferably, a chlorine atom is employed as a substituent on the heterocyclic group.

In Formula (1), "X" denotes a sulfur atom or $CH_2$, NR, and "R" denotes a hydrogen atom or an alkyl group. The alkyl group is a C1 to C4 alkyl group which may be any of primary, secondary and tertiary groups, and may for example be a methyl group, an ethyl group, an n-propyl group, an i-propyl group, an n-butyl group, an i-butyl group, a sec-butyl group, and a tert-butyl group.

In Formula (1), when "Y" is $COR_1$, "$R_1$" denotes a hydrogen atom or a C1 to C5 alkyl group, a halogenated methyl except for a trifluoromethyl group, a C2 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C4)alkoxy(C1 to C5)alkyl group, a C1 to C3 alkoxy carbonyl group, a (C1 to C3)alkylsulfonyl(C1 to C3)alkyl group, a (C1 to C3)alkylthio(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a cyano(C1 to C3)alkyl group, a substituted or unsubstituted phenoxy(C1 to C3)alkyl group, a substituted or unsubstituted pyridylmethyl group, a substituted or unsubstituted imidazolylmethyl group, a furanyl group, a morpholino group, a norbornenyl group, an adamantyl group, an isothiocyanatomethyl group, or a substituted or unsubstituted heterocyclic or aromatic ring.

The C1 to C5 alkyl group may be any of primary, secondary and tertiary groups, and may for example be a methyl group, an ethyl group, an n-propyl group, an i-propyl group, an n-butyl group, an i-butyl group, a sec-butyl group, and a tert-butyl group. The alkyl group in the C2 to C5 halogenated alkyl group may be any of primary, secondary, and tertiary groups, and may for example be an ethyl group, an n-propyl group, an i-propyl group, an n-butyl group, an i-butyl group, a sec-butyl group, and a tert-butyl group. The C3 to C7 substituted or unsubstituted cycloalkyl group may for example be a cyclopropyl group, a cyclobutyl group, a cyclopentyl group, and a cyclohexyl group. The substituent is not limited particularly, and may for example be a halogen atom (any of chlorine, bromine, fluorine and iodine) or a C1 to C3 alkyl group. The 3-membered to 7-membered substituted or unsubstituted heterocycloalkyl group is desirably a heterocycloalkyl group containing 1 to 2 heteroatoms such as oxygen atoms or sulfur atoms, nitrogen atoms. The substituent is not limited particularly, and may for example be a halogen atom (any of chlorine, bromine, fluorine and iodine) or a C1 to C3 alkyl group. The substituent substituting on the phenyl group in the substituted phenoxy(C1 to C3)alkyl group is not limited particularly, and may for example be a halogen atom (any of chlorine, bromine, fluorine and iodine) or a C1 to C3 alkyl group. The substituent attaching to the pyridine ring in the substituted pyridylmethyl group or the imidazole ring in the substituted imidazolylmethyl group is not limited particularly, and may for example be a halogen atom (any of chlorine, bromine, fluorine, and iodine) or a C1 to C3 alkyl group. Typical examples of the 5-membered and 6-membered heterocyclic ring include a quinoline ring, an indole ring, a pyridine ring, a pyrazine ring, a pyridazine ring, a pyrimidine ring, a thiophene ring, a thiazole ring, a tetrahydrofuran ring, and a furan ring. Those especially preferred are a 3-pyridyl group, a 5-thiazolyl group, and a 3-tetrahydrofuryl group. The substituent on the heterocyclic ring or an aromatic ring is not limited particularly and may for example be a halogen atom (any of fluorine, chlorine, bromine, and iodine), a C1 to C4 alkyl group, a C1 to C4 halogenated alkyl group, a C1 to C4 alkoxy group, a di(C1 to C4 alkyl)amino group, a nitro group, and an acetylamino group.

It is preferred especially that "$R_1$" is a trichloromethyl group, a methyl group, a chloromethyl group, a difluoromethyl group, a methoxymethyl group, a 2-methylthioethyl group, a cyclopropyl group, a 2,2-difluorocyclopropyl group.

In Formula (1), when "Y" is $CONR_3R_4$, each of "$R_3$" and "$R_4$" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a C1 to C3 alkoxy group, a substituted or unsubstituted C6 to C10 aryl group, a substituted or unsubstituted (C6 to C10) aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group; "$NR_3R_4$" may form a ring.

The C1 to C5 alkyl group may be any of primary, secondary, and tertiary groups, and may desirably be a methyl group, an ethyl group, an n-propyl group, an i-propyl group, an n-butyl group, an i-butyl group, a sec-butyl group, a tert-butyl group and the like. The C1 to C5 halogenated alkyl group may be any of primary, secondary, and tertiary groups, and may desirably be a methyl group, an ethyl group, an n-propyl group, an i-propyl group, an n-butyl group, an i-butyl group, a sec-butyl group, a tert-butyl group and the like. The C3 to C7 substituted or unsubstituted cycloalkyl group may for example be a cyclopropyl group, a cyclobutyl group, a cyclopentyl group, and a cyclohexyl group. The substituent is not limited particularly, and may for example be a halogen atom (any of chlorine, bromine, fluorine, and iodine) or a C1 to C3 alkyl group. The 3-membered to 7-membered substituted or unsubstituted heterocycloalkyl group is desirably a heterocycloalkyl group containing 1 to 2 heteroatoms such as oxygen atoms or sulfur atoms, nitrogen atoms. The substituent is not limited particularly, and may for example be a halogen atom (any of chlorine, bromine, fluorine, and iodine) or a C1 to C3 alkyl group. The substituent attaching to the pyridine ring in the substituted pyridylmethyl group is not limited particularly, and may for example be a halogen atom (any of chlorine, bromine, fluorine, and iodine) or a C1 to C3 alkyl group. The substituent attaching to the benzene ring in the substituted benzene sulfonyl group is not limited particularly, and may for example be a halogen atom (any of chlorine, bromine, fluorine, and iodine) or a nitro group, a di(C1 to C4 alkyl)amino group, an acetylamino group, a C1 to C3 alkyl group. When "$NR_3R_4$" forms a ring, each of $R_3$ and $R_4$ is preferably a C2 to C6 cyclic structure or a 3-membered to 7-membered cyclic structure containing, in the ring of the 3-membered to 7-membered ring represented as $NR_3R_4$, 1 to 2 heteroatoms such as oxygen atoms or sulfur atoms, nitrogen atoms.

Especially preferably, "$CONR_3R_4$" has, as its "$NHR_4$" moiety, a methoxylamino group or an ethoxylamino group.

In Formula (1), when "Y" is $CONHCOR_5$, "$R_5$" denotes a hydrogen atom or a C1 to C5 alkyl group, a C1 to C5 halogenated alkyl group, a C2 to C5 alkenyl group, a C2 to C5 halogenated alkenyl group, a substituted or unsubstituted C6 to C10 aryl group, a substituted or unsubstituted (C6 to C10) aryl(C1 to C3)alkyl group, a substituted or unsubstituted phenyl group.

The C1 to C5 alkyl group may be any of primary, secondary and, tertiary groups, and may for example be a methyl group, an ethyl group, an n-propyl group, an i-propyl group, an n-butyl group, an i-butyl group, a sec-butyl group, and a tert-butyl group. The C1 to C5 halogenated alkyl group may be any of primary, secondary, and tertiary groups, and may desirably be a methyl group, an ethyl group, an n-propyl group, an i-propyl group, an n-butyl group, an i-butyl group, a sec-butyl group, a tert-butyl group and the like. The C3 to C7 substituted or unsubstituted cycloalkyl group may for example be a cyclopropyl group, a cyclobutyl group, a cyclopentyl group, and a cyclohexyl group. The substituent is not limited particularly, and may for example be a halogen atom (any of chlorine, bromine, fluorine, and iodine) or a C1 to C3 alkyl group. The substituent attaching to the benzene ring in the substituted phenyl group is not limited particularly, and may for example be a halogen atom (any of chlorine, bromine, fluorine, and iodine) or a nitro group, a di(C1 to C4 alkyl)amino group, an acetylamino group, a C1 to C3 alkyl group.

In Formula (1), when "Y" is $CO_2R_9$, "$R_9$" denotes a hydrogen atom or a C1 to C7 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a (C1 to C3)alkylthio(C1 to C3)alkyl group, a tri(C1 to C3 alkyl)silyl(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a substituted or unsubstituted phenyl group, a substituted or unsubstituted phenylmethyl group, a substituted or unsubstituted furanylmethyl group, a substituted or unsubstituted thienylmethyl group, a substituted or unsubstituted pyridylmethyl group, a succinimide group, a 18-crown-6-methyl group. The C1 to C7 alkyl group may be any of primary, secondary, and tertiary groups, and may for example be a methyl group, an ethyl group, an n-propyl group, an i-propyl group, an n-butyl group, an i-butyl group, a sec-butyl group, a tert-butyl group, an n-pentyl group, and an n-hexyl group. The alkyl group in the C1 to C5 halogenated alkyl group may be any of primary, secondary, and tertiary groups, and may for example be a methyl group, an ethyl group, an n-propyl group, an i-propyl group, an n-butyl group, an i-butyl group, a sec-butyl group, and a tert-butyl group. The C3 to C7 substituted or unsubstituted cycloalkyl group may for example be a cyclopropyl group, a cyclobutyl group, a cyclopentyl group, and a cyclohexyl group. The substituent is not limited particularly, and may for example be a halogen atom (any of chlorine, bromine, fluorine, and iodine) or a C1 to C3 alkyl group. The 3-membered to 7-membered substituted or unsubstituted heterocycloalkyl group is desirably a heterocycloalkyl group containing 1 to 2 heteroatoms such as oxygen atoms or sulfur atoms, nitrogen atoms. The substituent is not limited particularly, and may for example be a halogen atom (any of chlorine, bromine, fluorine, and iodine) or a C1 to C3 alkyl group. The substituent substituting on the phenyl group in the substituted phenyl group is not limited particularly, and may for example be a halogen atom (any of fluorine, chlorine, bromine, and iodine), a C1 to C4 alkyl group, a C1 to C4 halogenated alkyl group, a C1 to C4 alkoxy group, a di(C1 to C4 alkyl)amino group, a nitro group, and an acetylamino group. The substituent attaching to the phenyl ring, the furan ring, the thiophene ring, the pyridine ring, the imidazole ring in the substituted phenylmethyl group or the substituted furanyl methyl group, the substituted thienylmethyl group, the substituted pyridylmethyl group, the substituted imidazolylmethyl group is desirably a halogen atom (any of chlorine, bromine, fluorine, and iodine), a C1 to C3 alkyl group, and the like.

It is especially preferable that "$R_9$" is an n-propyl group, an i-propyl group, a 2-chloroethyl group, an ethyl group, a 2-fluoroethyl group, a 2,2-difluoroethyl group, a 2-methoxyethyl group, a 2-methylthioethyl group, a 3-fluoropropyl group, a 2-propenyl group, an n-butyl group, an i-butyl group, a sec-butyl group, a 3-methyl-2-butenyl group, an n-pentyl group, a cyclopropylmethyl group, a 3-oxetanyl group, a 3-tetrahydrofuranylmethyl group, or a 4-tetrahydropyranyl group.

The carbon chain in Formula (1) described above may be substituted with halogens.

A novel imino derivative according to the invention has excellent insecticidal activity, acaricidal activity and the like against a broad range of agricultural pests and household pests. Accordingly, it can be used as a pesticide containing such compounds as an active ingredient, such as an insecticide or acaricide against agricultural pests and household pests and as a domestic pest-controlling agent, such as termite-controlling agent, as well as a veterinary pharmaceutical.

(B) Methods for Producing Novel Imino Derivatives

A method for producing a novel imino derivative according to the invention is described below.

(1) First Step

In the first step of this production method, a compound represented by Formula (4) is produced by reacting a compound represented by Formula (2) with a compound (3) represented by Formula (3) in the presence of a base. The reaction scheme of the first step is shown in FIG. 1.

Formula (2)

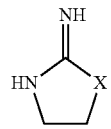

[C.13]

wherein "X" denotes a sulfur atom or $CH_2$, NR; "R" denotes a hydrogen atom or an alkyl group.

[C.14]

$ArCH_2Z$            Formula (3)

wherein "Ar" denotes a heterocyclic group which may have a substituent on the ring; "Z" denotes Cl or Br, I, $OSO_2CH_3$, $OSO_2C_6H_5$, $OSO_2C_6H_4CH_3$;

Formula (4)

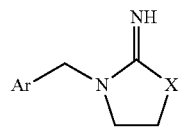

[C.15]

wherein "Ar" denotes a heterocyclic group which may have a substituent on the ring; "X" denotes a sulfur atom or $CH_2$, NR; "R" denotes a hydrogen atom or an alkyl group.

In the first step, 1 mole of the compound represented by Formula (4) can be produced by reacting 1 mole of the compound represented by Formula (2) with 1.0 to 1.5 moles of a halogeneted compound represented by Formula (3).

In the first step, the amount of the compound (3) represented by Formula (3) to be added is preferably 1.0 to 1.1 moles per mole of the compound (2) described above.

This compound (4) may be synthesized by a known production method (for example, Journal of Medical Chemistry, 1999, 42(12), 2227-2234) or a method analogous thereto.

While the type of the base employed in the first step is not limited particularly, it is preferably an alkaline metal hydride such as sodium hydride (NaH), a carbonate such as potassium carbonate ($K_2CO_3$) or sodium carbonate ($Na_2CO_3$), an alkaline metal hydroxide such as potassium hydroxide (KOH), sodium hydroxide (NaOH), tertiary amines such as triethylamine [$(C_2H_5)_3N$] and the like.

It is preferred in the first step to use a solvent, which may for example be amides such as dimethyl formamide (DMF) and dimethyl acetamide, nitriles such as acetonitrile, sulfoxides such as dimethyl sulfoxide (DMSO), ethers such as diethyl ether and tetrahydrofuran (THF), aromatic hydrocarbons such as benzene, xylene, and toluene, alcohols such as ethanol and propanol, ketones such as acetone and methylethylketone, aliphatic hydrocarbons such as hexane, heptane, and octane, halogenated hydrocarbons such as dichloromethane, chloroform, chlorobenzene, and dichlorobenzene, and water, which may be employed alone or in combination of one or more thereof.

To the reaction mixture, a phase transfer catalyst including a quaternary ammonium salt such as tetrabutylammonium salt or a crown ether or analogues thereto may be added to proceed these reactions. In such a case, the solvent employed is not limited particularly, and the oil phase may be benzene, chloroform, dichloromethane, hexane, toluene and the like.

The reaction temperature in the first step is preferably 0 to 200° C. A reaction temperature below 0° C. results in a slow reaction rate, while that exceeding 200° C. results in a too rapid reaction rate, which is disadvantageous since it allows a side reaction to be proceeded easily. The reaction time in the first step may appropriately be selected based on the temperature condition and the pressure condition, and it is preferably within the range of 30 minutes to 24 hours.

(2-1) Second Step (I)

Figure 2:
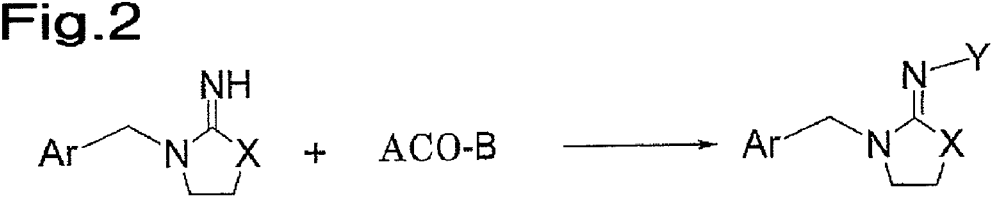
FIG. 2 shows a reaction scheme of the second step (I) of the method for producing the novel imino derivative according to the invention.

In the second step of this production method, a compound (1), which is an imino derivative represented by Formula (1) shown above wherein "Y" is defined similarly to "ACO", is produced by reacting a compound (5) represented by Formula (5) with a compound represented by Formula (4) obtained in the first step in the presence of a base. The reaction scheme of the second step (I) is shown in FIG. 2.

[C.16]

ACO—B          Formula (5)

wherein "B" denotes a halogen atom of Cl or Br, I, an OCOA group (a group formed by allowing each of an oxygen atom and a group A to form a single bond with a carbonyl group (CO)) or a hydroxyl group; when "ACO" is $COR_1$, "$R_1$" denotes a hydrogen atom or a C1 to C5 alkyl group, a halogenated methyl except for a trifluoromethyl group, a C2 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C4)alkoxy(C1 to C5)alkyl group, a C1 to C3 alkoxy carbonyl group, a (C1 to C3)alkylsulfonyl(C1 to C3)alkyl group, a (C1 to C3)alkylthio(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a cyano(C1 to C3)alkyl group, a substituted or unsubstituted phenoxy(C1 to C3)alkyl group, a substituted or unsubstituted pyridylmethyl group, a substituted or unsubstituted imidazolylmethyl group, a furanyl group, a morpholino group, a norbornenyl group, an adamantyl group, an isothiocyanatomethyl group, or substituted or unsubstituted heterocyclic or aromatic ring;

when "ACO" is $CONR_3R_4$, each of "$R_3$" and "$R_4$" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a C1 to C3 alkoxy group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group; "$NR_3R_4$" may form a ring;

when "ACO" is $CO_2R_9$, "$R_9$" denotes a hydrogen atom or a C1 to C7 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a (C1 to C3)alkylthio(C1 to C3)alkyl group, a tri(C1 to C3 alkyl)silyl(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a substituted or unsubstituted phenyl group, a substituted or unsubstituted phenylmethyl group, a substituted or unsubstituted furanylmethyl group, a substituted or unsubstituted thienylmethyl group, a substituted or unsubstituted pyridylmethyl group, a succinimide group, a 18-crown-6-methyl group.

In the second step (I), 1 mole of the novel imino derivative represented by Formula (1) can be produced by reacting 1 mole of the compound represented by Formula (4) with 1 to 2 moles of a halogenated compound represented by Formula (5).

In the second step (I), the amount of the compound (5) represented by Formula (5) to be added is preferably 1.0 to 1.2 moles per mole of the compound represented by Formula (4).

While the type of the base employed in the second step (I) is not limited particularly, it is preferably an alkaline metal hydride such as sodium hydride (NaH), a carbonate such as potassium carbonate ($K_2CO_3$) or sodium carbonate ($Na_2CO_3$), an alkaline metal hydroxide such as potassium hydroxide (KOH), sodium hydroxide (NaOH), tertiary amines such as triethylamine [$(C_2H_5)_3N$] and the like.

It is desirable in the second step (I) to use a solvent, which may for example be amides such as dimethyl formamide (DMF) and dimethyl acetamide, nitriles such as acetonitrile, sulfoxides such as dimethyl sulfoxide (DMSO), ethers such as diethyl ether and tetrahydrofuran (THF), aromatic hydrocarbons such as benzene, xylene, and toluene, alcohols such as ethanol and propanol, ketones such as acetone and methylethylketone, aliphatic hydrocarbons such as hexane, heptane, and octane, halogenated hydrocarbons such as dichloromethane, chloroform, chlorobenzene, and dichlorobenzene, and water, which may be employed alone or in combination of one or more thereof.

To the reaction mixture in the second step (I), a phase transfer catalyst including a quaternary ammonium salt such as tetrabutylammonium salt or a crown ether or analogues thereto may be added to proceed these reactions. In such a case, the solvent employed is not limited particularly, and the oil phase may be benzene, chloroform, dichloromethane, hexane, toluene and the like.

The reaction temperature in the second step (I) is preferably 0 to 200° C. A reaction temperature below 0° C. results in a slow reaction rate, while that exceeding 200° C. results in a too rapid reaction rate, which is disadvantageous since it allows a side reaction to be proceeded easily. While the reaction in the second step (I) can be conducted under reduced pressure, at ambient temperature, or under pressure, it is conducted preferably at ambient temperature. The reaction time in the second step (I) may appropriately be selected based on the temperature condition and the pressure condition, and it is preferably within the range of 30 minutes to 24 hours.

In the second step (I) of this production method, an imino derivative represented by Formula (1) shown above can be produced also by reacting an anhydride represented by Formula (6) or a carboxylic acid represented by Formula (7), instead of the halogenated compound represented by Formula (5), with a compound represented by Formula (4) obtained in the first step in the presence of a base.

[C.17]

ACOOCOA                    Formula (6)

[C.18]

ACOOH                       Formula (7)

When using a carboxylic acid represented by Formula (7), a dehydrating condensation agent such as dicyclohexyl carbodiimide, 1-alkyl-2-halopyridinium salt, 1,1-carbonium imidazole, 1-ethyl-3-(3-dimethylaminopropyl)carbodiimide hydrochloride is employed in the presence of a base.

(2-2) Second Step (II)

Figure 3:
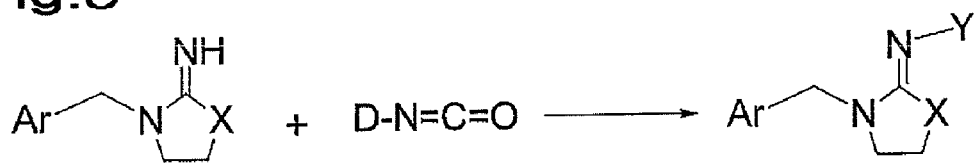
FIG. 3 shows a reaction scheme of the second step (II) of the method for producing the novel imino derivative according to the invention.

In the second step of this production method, an imino derivative represented by Formula (9) may be produced by reacting an isocyanate compound represented by Formula (8) with a compound represented by Formula (4) shown above in the presence of a base. The reaction scheme of the second step (II) is shown in FIG. 3.

[C.19]

D-N=C=O                     Formula (8)

wherein "D" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group, $COR_5$; "$R_5$" denotes a hydrogen atom or a C1 to C5 alkyl group, a C1 to C5 halogenated alkyl group, a C2 to C5 alkenyl group, a C2 to C5 halogenated alkenyl group, a substituted or unsubstituted C6 to C10 aryl group, a substituted or unsubstituted (C6 to C10)aryl(C1 to C3)alkyl group, a substituted or unsubstituted phenyl group.

Formula (9)

[C.20]

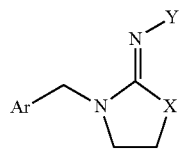

wherein "Ar" denotes a heterocyclic group which may have a substituent on the ring; "X" denotes a sulfur atom or $CH_2$, NR; "R" denotes a hydrogen atom or an alkyl group; "Y" denotes "CONHD", "D" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group, or $COR_5$; "$R_5$" denotes a hydrogen atom or a C1 to C5 alkyl group, a C1 to C5 halogenated alkyl group, a C2 to C5 alkenyl group, a C2 to C5 halogenated alkenyl group, a substituted or unsubstituted C6 to C10 aryl group, a substituted or unsubstituted (C6 to C10)aryl(C1 to C3)alkyl group, a substituted or unsubstituted phenyl group.

In the second step (II), 1 mole of the novel imino derivative represented by Formula (9) can be produced by reacting 1 mole of the compound represented by Formula (4) with 1 mole of an isocyanate compound represented by Formula (8).

In the second step (II), the amount of the isocyanate compound represented by Formula (8) to be added is preferably 1.0 to 1.2 moles per mole of the compound represented by Formula (4) described above.

While the type of the base employed in the second step (II) is not limited particularly, it is preferably an alkaline metal hydride such as sodium hydride (NaH), a carbonate such as potassium carbonate ($K_2CO_3$) or sodium carbonate ($Na_2CO_3$), an alkaline metal hydroxide such as potassium hydroxide (KOH), sodium hydroxide (NaOH), tertiary amines such as triethylamine [$(C_2H_5)_3N$] and the like.

It is desirable in the second step (II) to use a solvent, which may for example be amides such as dimethyl formamide (DMF) and dimethyl acetamide, nitriles such as acetonitrile, sulfoxides such as dimethyl sulfoxide (DMSO), ethers such as diethyl ether and tetrahydrofuran (THF), aromatic hydrocarbons such as benzene, xylene, and toluene, alcohols such as ethanol and propanol, ketones such as acetone and methylethylketone, aliphatic hydrocarbons such as hexane, heptane, and octane, halogenated hydrocarbons such as dichloromethane, chloroform, chlorobenzene, and dichlorobenzene, and water, which may be employed alone or in combination of one or more thereof.

To the reaction mixture in the second step (II), a phase transfer catalyst including a quaternary ammonium salt such as tetrabutylammonium salt or a crown ether or analogues thereto may be added to proceed these reactions. In such a case, the solvent employed is not limited particularly, and the oil phase may be benzene, chloroform, dichloromethane, hexane, toluene and the like.

The reaction temperature in the second step (II) is preferably 0 to 200° C. A reaction temperature below 0° C. results in a slow reaction rate, while that exceeding 200° C. results in a too rapid reaction rate, which is disadvantageous since it allows a side reaction to be proceeded easily. While the reaction in the second step (II) can be conducted under reduced pressure, at ambient temperature, or under pressure, it is preferably conducted at ambient temperature. The reaction time in the second step (II) may appropriately be selected based on the temperature condition and the pressure condition, and it is preferably within the range of 30 minutes to 24 hours.

(2-3) Second Step (III)

Figure 4:
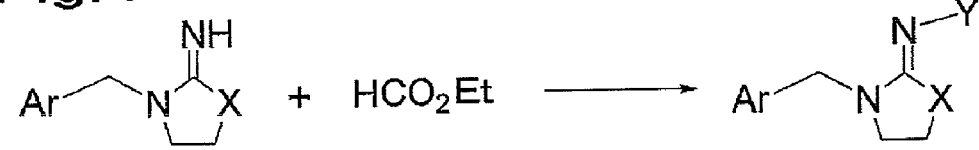
FIG. 4 shows a reaction scheme of the second step (III) of the method for producing the novel imino derivative according to the invention.

Moreover, in the second step of this production method, an imino derivative represented by Formula (11) may be produced by reacting a formate represented by Formula (10) with a compound represented by Formula (4) shown above in the presence of a base. The reaction scheme of the second step (III) is shown in FIG. 4.

[C.21]

HCO₂Et                                                    Formula (10)

Formula (11)

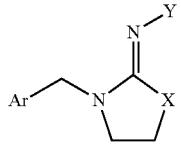

[C.22]

wherein "Ar" denotes a heterocyclic group which may have a substituent on the ring; "X" denotes a sulfur atom or CH₂, NR; "R" denotes a hydrogen atom or an alkyl group; "Y" denotes CHO.

In the second step (III), 1 mole of the novel imino derivative represented by Formula (11) can be produced by reacting 1 mole of the compound represented by Formula (4) with 1 mole of a formate represented by Formula (10).

In the second step (III), the amount of the formate represented by Formula (10) to be added is preferably 1 to 1.2 moles per mole of the compound represented by Formula (4) described above.

While the type of the base employed in the second step (III) is not limited particularly, it is preferably an alkaline metal hydride such as sodium hydride (NaH), a carbonate such as potassium carbonate ($K_2CO_3$) or sodium carbonate ($Na_2CO_3$), an alkaline metal hydroxide such as potassium hydroxide (KOH), sodium hydroxide (NaOH), tertiary amines such as triethylamine [$(C_2H_5)_3N$] and the like.

It is desirable in the second step (III) to use a solvent, which may for example be amides such as dimethyl formamide (DMF) and dimethyl acetamide, nitriles such as acetonitrile, sulfoxides such as dimethyl sulfoxide (DMSO), ethers such as diethyl ether and tetrahydrofuran (THF), aromatic hydrocarbons such as benzene, xylene, and toluene, alcohols such as ethanol and propanol, ketones such as acetone and methylethylketone, aliphatic hydrocarbons such as hexane, heptane, and octane, halogenated hydrocarbons such as dichloromethane, chloroform, chlorobenzene, and dichlorobenzene, and water, which may be employed alone or in combination of one or more thereof.

To the reaction mixture in the second step (III), a phase transfer catalyst including a quaternary ammonium salt such as tetrabutylammonium salt or a crown ether or analogues thereto may be added to proceed these reactions. In such a case, the solvent employed is not limited particularly, and the oil phase may be benzene, chloroform, dichloromethane, hexane, toluene and the like.

The reaction temperature in the second step (III) is preferably 0 to 200° C. A reaction temperature below 0° C. results in a slow reaction rate, while that exceeding 200° C. results in a too rapid reaction rate, which is disadvantageous since it allows a side reaction to be proceeded easily. While the reaction in the second step (III) can be conducted under reduced pressure, at ambient temperature, or under pressure, it is preferably conducted at ambient temperature. The reaction time in the second step (III) may appropriately be selected based on the temperature condition and the pressure condition, and it is preferably within the range of 30 minutes to 24 hours.

The first step and the second steps (I) to (III) can also be conducted continuously while skipping a step for isolating the intermediate which is a compound represented by Formula (4). In such a case, after completing the first step, certain amounts of the halogenated compound represented by Formula (5) and the base employed in the second step are added, and a certain reaction temperature is established, whereby allowing the reaction of the second step to be carried out consecutively.

A compound (1) wherein "Y" is "$CONR_3R_4$" [$CONR_3R_4$ in which $R_3$ is a hydrogen or a C1 to C5 alkyl group and $R_4$ is a C1 to C3 alkoxy group, preferably CON(hydrogen or methyl)(C1 to C3-alkoxy) group, more preferably, methoxylaminocarbonyl, ethoxylaminocarbonyl] can be produced by reacting a compound wherein "Y" is "$CO_2R_9$" in which "$R_9$" is a substituted or unsubstituted phenyl group (for example, 4-nitrophenyl group) with an O-alkylhydroxylamine, an N,O-dialkylhydroxylamine or salts thereof in the presence of a base (for example, sodium acetate, or potassium carbonate) in a solvent (for example, acetonitrile).

By using a production method according to the invention described above, a novel imino derivative represented by Formula (1) according to the invention can be produced using as a starting material a substance which has a relatively high versatility.

(C) Insecticides

A novel imino derivative according to the invention can be preferably employed as an insecticide. An agro-horticultural insecticide containing a novel imino derivative represented by Formula (1) as an active ingredient is discussed below.

Agricultural pests against which an inventive insecticide can exert its controlling effect are listed below. Lepidoptera pests may for example be oriental corn borer (*Ostrinia furnacalis*), Oriental armyworm moth (*Pseudaletia separata*), pink borer (*Sesamia inferens*), corn earworm (*Heliothis* sp.), turnip moth (*Agrotis segetum*), apple leafminer (*Phyllonorycter ringoniella*), diamondback moth (*Plutella xylostella*), rice leafroller (*Cnaphalocrocis medinalis*), yellow stemborer (*Scirpophaga incertulas*), beet armyworm (*Spodoptera exigua*), rice stem borer (*Chilo suppressalis*), common cutworm (*Spodoptera litura*), soybean pod borer (*Leguminivora glycinivorella*), peach fruit moth (*Carposina niponensis*), common cabbage worm (*Piers rapae crucivora*), summer fruit tortrix (*Adoxophyes orana fasciata*), and cabbage armyworm (*Mamestra brassicae*), Hemiptera pests may for example be greenhouse whitefly (*Trialeurodes vaporariorum*), sweetpotato whitefly (*Bemisia tabaci*), green rice leafhopper (*Nephotettix cincticeps*), brown rice planthopper (*Nilaparvata lugens*), turnip aphid (*Lipaphis erysimi*), citrus psyllid (*Diaphorina citri*), cottony citrus scale (*Pulvinaria aurantii*), green peach aphid (*Myzus persicae*), arrowhead scale (*Unaspis yanonensis*), and cotton aphid (*Aphis gossypii*). Coleoptera pests may for example be bean beetle (*Callosobruchus chinensis*), rice leaf beetle (*Oulema oryzae*), rice water weevil (*Lissorhoptrus oryzophilus*), cucurbit leaf beetle (*Aulacophora femoralis*), striped flea beetle (*Phyllotreta striolata*), Maize weevil (*Sitophilus zeamais*), cigarette beetle (*Lasioderma serricorne*), twenty-eight-spotted ladybird (*Epilachna vigintiotopunctata*), soybean beetle (*Anomala rufocuprea*), Brown powder-post beetle (*Lyctus brunneus*), and Japanese beetle (*Popillia japonica*), Thysanoptera pests may for example be onion thrips (*Thripstabaci*), melon thrips (*Thrips palmi*), and rice thrips (*Stenchaetothrips biformis*), Diptera pests may for example be house mosquito (*Culexpipiens*), House Fly (*Musca domestica*), rice leafminer (*Agromyza oryzae*), Melon fly (*Dacus*(*Zeugodacus*) *cucurbitae*), soybean pod gall midge (*Asphondylia* sp.), onion maggot (*Delia antiqua*), seedcorn maggot (*Delia platura*), and oriental fruit fly (*Dacus*(*Bactrocera*) *dorsalis*), Dyctyoptera pests may for example be German cockroach (*Batella germanica*), Orental termite (*Coptotermes formosanus*), and Japanese subterranean termite (*Reticulitermes speratus*), Orthoptera pests may for example be Migratory locust (*Locusta migratoria*), Acari pests may for example be two-spotted spider mite (*Tetranychus urticae*), kanzawa spider mite (*Tetranychus kanzawai*), and citrus red mite (*Panonychus citri*), acarian pests parasiting animals may for example be soft tick (*Ornithodoros*), fleas may for example be cat flea (*Ctenocephalides felis*) and dog flea (*Ctenocephalides canis*), lice may for example be poultry lice (*Menopon*), and Trematoda, Cestoda, Nematoda, and Coccidia may also be exemplified.

Methods for using the insecticides according to the invention is not limited particularly, and it may be used as it is or as being diluted to a desired concentration with a diluent such as water. It is also possible to use several types of 6-membered heterocyclic derivatives according to the invention in combination, and a mixture with other pesticides may also be employed as long as the effects of the insecticides are not affected adversely. Other pesticides which may be employed in a mixture are not limited particularly, and may for example be other fungicides, insecticides, acaricides, herbicides, plant growth regulators, fertilizers and the like.

When using an inventive insecticide as being diluted, the concentration of the novel imino derivative is preferably within the range of 0.001 to 1.0%. The treatment rate of the inventive insecticide is adjusted in such a manner that 1 ha of an agro-horticultural site such as a field, a paddy field, an orchard, and a greenhouse is treated preferably with 20 to 5000 g, more preferably with 50 to 1000 g of a novel imino derivative. Such concentration and treatment rate are not limited to those specified above, and may appropriately be increased or decreased depending on the dosage form, the timing of use, the method of use, the site of use, the crops to be treated and the like.

The insecticide according to the invention is used as a formulation in which a novel imino derivative and a carrier are mixed. If necessary, various formulation auxiliaries, such as a surfactant, a spreading agent, a depositing agent, a thickening agent, and a stabilizer, may further be incorporated to formulate a dosage form such as a wettable powder, a granule, and a flowable formulation.

In the insecticide according to the invention, when a novel imino derivative is mixed with a carrier, the amount of the carrier is usually within the range of 0.1 to 80% by weight. The carriers for the formulations mentioned above include microparticulate or granulate solid carriers such as kaolin, attapulgite, bentonite, acid clay, pyrophyllite, talc, kieselguhr, calcite, ground walnut powder, urea, ammonium sulfate, and synthetic hydrated silicon oxide, aromatic hydrocarbons such as xylene and naphthalene, alcohols such as isopropanol, ethylene glycol, and cellosolve, ketones such as acetone, cyclohexanone, and isophorone, vegetable oils such as soybean oil and cottonseed oil, liquid carriers such as dimethyl sulfoxide, acetonitrile, and water.

The surfactant employed for emulsification, dispersion, and spreading may for example be an anionic surfactant such as an alkyl sulfate salt, an alkyl(aryl)sulfonate, a dialkylsulfosuccinate, a polyoxiethylene alkylaryl ether phosphate salt, a naphthalenesulfonic acid formaldehyde condensate, and a polycarboxylic acid-type polymer, and a nonionic surfactant such as a polyoxyethylene alkyl ether, a polyoxyethylene alkylaryl ether, a polyoxyethylene polyoxypropylene block copolymer, and a sorbitan fatty acid ester. The formulation auxiliaries may for example be a lignin sulfonate, alginate, a polyvinylalcohol, gum arabic, CMC (carboxymethyl cellulose), PAP (acidic isopropyl phosphate), and xanthane gum.

The insecticide capable of being mixed with an insecticide according to the invention may for example be an organic phosphorus-based insecticide (fenitrothion, malathion, acephate, diazinon and the like), a carbamate-based insecticide (benfuracarb, methomyl, carbosulfan and the like), a pyrethroid-based insecticide (allethrin, permethrin, fenvalerate, etofenprox, silafluofen and the like), a nereistoxin-based insecticide (cartap, thiocyclam and the like), a neo-nicotinoide-based insecticide (imidacloprid, acetamiprid, thiamethoxam, dinotefuran and the like), an IGR agent (diflubenzuron, cyromazine and the like), fipronil, emamectin benzoate, pyridalyl, propylene glycol fatty acid monoester, and a BT agent, a bacteriocide capable of being mixed may for example be a copper fungicide (inorganic copper, organic copper, nonylphenylether copper sulfonate and the like), an inorganic sulfur agent, an organic sulfur fungicide (maneb, manzeb, amobam, propineb, thiuram and the like), an organic phosphorus-based fungicide (fosethyl, tolclofos-methyl and the like), a melanin biosynthesis inhibitor (fthalide, tricyclazole, pyroquilon, carpropamid, diclocymet, fenoxanil), a benzimidazol-based fungicide (thiophanate-methyl, benomyl, diethofencarb, and the like), a dicarboxylmide agent (iprodione, procymidone and the like), an acid amid-based fungicide (mepronil, flutolanil, boscalid, furametpyr, thifluzamide, metalaxyl- and the like), a sterol biosynthesis inhibitor (triflumizole, tebuconazole, ipconazole, metconazole, epoxiconazole and the like), a strobilurin-based fungicide (azoxystrobin, kresoxim-methyl, trifloxystrobin and the like), an anilinopyrimidine-based fungicide (mepanipyrim, cyprodinil and the like), an antibacterial agent (oxolinic acid, tecloftalam and the like), an antibiotic fungicide (kasugamycin, polyoxins, streptomycin and the like), probenazole, ferimzone, TPN, fludioxonil, iminoctadine acetate, cyazofamid, and cyflufenamid, an acaricide capable of being mixed may for example be bifenazate, milbemectin, and etoxazole, a herbicide capable of being mixed may for example be a phenoxy acid-based herbicide (2,4-d, clomeprop, and fluazifop), a carbamate-based herbicide (benthiocarb, molinate, pyributicarb and the like), an acid amide-based herbicide (pretilachlor, diflufenican, mefenacet, cafenstrole, asulam and the like), an urea-based herbicide (daimuron, isouron and the like), a sulfonyl urea-based herbicide (imazosulfuron, thifensulfuron-methyl, nicosulfuron, halosulfuron methyl and the like), a triazine-based herbicide (atrazine, simetryn, simazine, triaziflam and the like), a diazine-based herbicide (bentazone, bromacil and the like), a diazole-based herbicide (pyrazolate, oxadiazon and the like), a bipyridylium-based herbicide (paraquat and the like), a dinitroaniline-based herbicide (trifluralin, pendimethalin, oryzalin and the like), an aromatic carboxylic acid-based herbicide (fentrazamide, imazapyr and the like), a pyrimidyloxy benzoate-based herbicide (bispyribac sodium and the like), a fatty acid-based herbicide (tetrapion and the like), an amino acid-based herbicide (glyphosate, glufosinate and the like), a nitrile-based herbicide (chlorthiamid and the like), a cyclogexadione-based herbicide (sethoxydim, clethodim and the like), a phenylphthalimide-based herbicide (chlorphthalim and the like), butamifos, pentoxazone, and benzobicyclon, a plant growth regulator capable of being mixed may for example be uniconazole p, daminozide, paraffin, wax, and benzylaminopurine, although the agents capable of being mixed or being a composite formulation with an inventive plant anthrax controller are not limited to those listed above.

EXAMPLES

Production Examples and Formulation Examples, as well as Experimental Examples of the novel imino derivatives and insecticides according to the invention are represented below whereby a detailed description of the invention is made. The invention is not limited to the below-indicated Production Examples and the like, as long as there is no departure from its scope. The compounds employed in the following Production Examples and the like may be any commercially available ones as appropriate. The measurement of the physical data of respective intended compound obtained in respective Examples was conducted under the condition indicated in "Table 1" shown below.

The intended compounds obtained in Examples of novel imino derivatives represented by Formula (1) shown above had the chemical structures and the melting points shown in "Table 2" to "Table 11", and the measured values of IR spectra and NMR spectra shown in "Table 12" to "Table 22". Among those, some Examples are detailed below with regard to Production Examples, Formulation Examples, and Experimental Examples.

TABLE 1

| | |
|---|---|
| Melting point | Measured using BUECHI Model B-545 |
| IR (Infrared spectroscopy) | Measured by KBr tablet method using HITACHI, Ltd. Model 270-30 |
| $^1$H-NMR (Proton nuclear magnetic resonance spectroscopy) | Measured by JEOL Ltd. device (400 MHz) using internal standard TMS (tetramethylsilane) and solvent DMSO-$d_6$ (tritylated dimethylsulfoxide) |

TABLE 2

| Compound No. | Y | Ar | X | Melting Point (° C.) |
|---|---|---|---|---|
| 1 | —COCF$_2$CF$_2$CF$_3$ | 2-Cl-pyridin-5-yl | S | Oil |
| 2 | —COCH$_2$CF$_3$ | 2-Cl-pyridin-5-yl | S | 88-90 |
| 3 | —COC(CH$_3$)$_3$ | 2-Cl-pyridin-5-yl | S | 45 |
| 4 | —COC(CF$_3$)$_2$CH$_3$ | 2-Cl-pyridin-5-yl | S | 114-116 |
| 5 | —COCCl$_3$ | 2-Cl-pyridin-5-yl | S | 90 |
| 6 | —CO-phenyl | 2-Cl-pyridin-5-yl | S | 133 |
| 7 | —CO-(4-Cl-phenyl) | 2-Cl-pyridin-5-yl | S | 185 |
| 8 | —CO-(4-CH$_3$-phenyl) | 2-Cl-thiazol-5-yl | S | 175 |
| 9 | —CO-cyclohexyl | 2-Cl-pyridin-5-yl | S | 196 |
| 10 | —CO—CH$_2$-phenyl | 2-Cl-pyridin-5-yl | S | 157-158 |

TABLE 2-continued

| Compound No. | Y | Ar | X | Melting Point (° C.) |
|---|---|---|---|---|
| 11 | quinolin-3-yl-CO | 6-chloropyridin-3-yl | S | 180-182 |
| 12 | 1H-indol-3-yl-CO | 6-chloropyridin-3-yl | S | 185-188 |
| 13 | pyridin-3-yl-CO | 6-chloropyridin-3-yl | S | 117-118 |
| 14 | pyrazin-2-yl-CO | 6-chloropyridin-3-yl | S | 157-158 |
| 15 | 6-chloropyridin-3-yl-CO | 6-chloropyridin-3-yl | S | 160-162 |
| 16 | 5-chloropyrazin-2-yl-CO | 6-chloropyridin-3-yl | S | 134-136 |
| 17 | 2,6-dichloropyridin-4-yl-CO | 6-chloropyridin-3-yl | S | 165-166 |
| 18 | pyridazin-4-yl-CO | 6-chloropyridin-3-yl | S | 204-206 |

TABLE 3

| 19 | 6-chloropyridin-2-yl-CO | 6-chloropyridin-3-yl | S | 128 |
| 20 | 5-bromopyridin-3-yl-CO | 6-chloropyridin-3-yl | S | 156-58 |
| 21 | 4-trifluoromethylpyridin-3-yl-CO | 6-chloropyridin-3-yl | S | 123-125 |
| 22 | 4,5-dichloropyridin-3-yl-CO | 6-chloropyridin-3-yl | S | 180-181 |
| 23 | 2,6-dichloropyridin-3-yl-CO | 6-chloropyridin-3-yl | S | 179-182 |
| 24 | pentafluorophenyl-CO | 6-chloropyridin-3-yl | S | 233 |

TABLE 3-continued
| | | | | |
|---|---|---|---|---|
| 28 | CONH₂ | 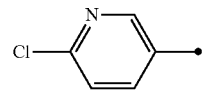 | S | 158-159 |
| 29 | CONHCH₃ | 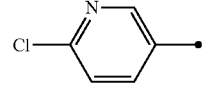 | S | 175-177 |
| 30 | CONHCH2CO2CH2CH3 | 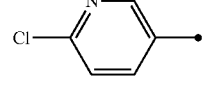 | S | 166-167 |
| 31 | CONHCOCH2Cl | 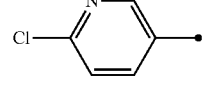 | S | 165-166 |
| 32 | 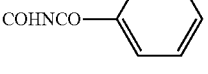 | 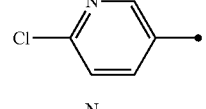 | S | 179-181 |
| 33 | 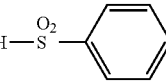 | 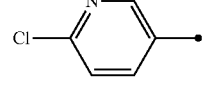 | S | 191-193 |
| 34 | CONHCH(CH₃)2 | 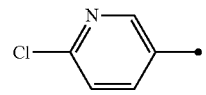 | S | 85 |
TABLE 3-continued
| | | | | |
|---|---|---|---|---|
| 35 | 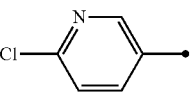 | 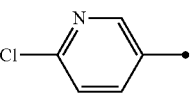 | S | 133-134 |
| 36 | 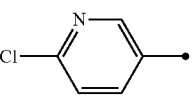 | 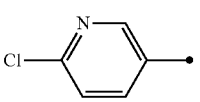 | S | 170-172 |
| 37 | 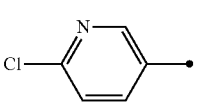 | 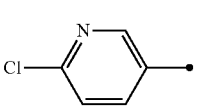 | S | 74-76 |
| 42 | CO2CH3 | 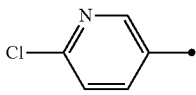 | S | 128-130 |
| 43 | CO2CH2CH2CH3 | 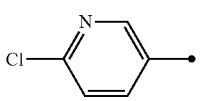 | S | 97-99 |
| 44 | CO2CH(CH3)2 | 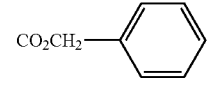 | S | 141-143 |
TABLE 4
| | | | | |
|---|---|---|---|---|
| 45 | CO2CH2CH2Cl | 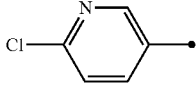 | S | 106-108 |
| 46 | CO2CH2CH2OCH3 | 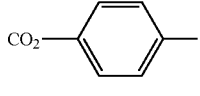 | S | 69-71 |
| 47 | 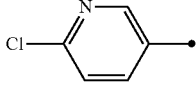 | 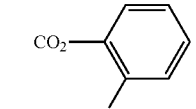 | S | 94-95 |
| 48 | 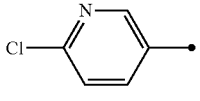 | 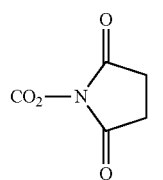 | S | 114-115 |
| 49 | 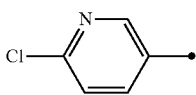 |  | S | Oil |
| 50 |  |  | S | 207-209 |

TABLE 4-continued
| | | | | |
|---|---|---|---|---|
| 51 | 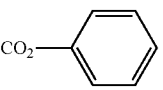 | 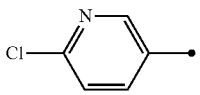 | S | 169 |
| 52 | CO2C6H13 | 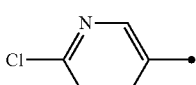 | S | 43 |
| 53 | 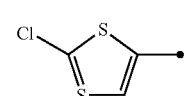 | 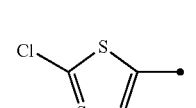 | S | 193 |
| 56 | COCCl3 | 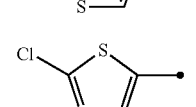 | S | Oil |
| 57 | 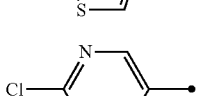 | 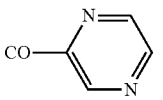 | S | 120 |
| 58 | CHO | 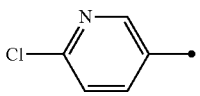 | S | 99-100 |
| 59 | CHO | 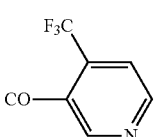 | CH2 | Oil |
| 60 | CHO |  | NH | Oil |
| 61 | CHO |  | S | 76 |
| 62 | CHO |  | CH2 | Oil |
| 63 |  |  | CH2 | 104-106 |
| 64 |  |  | CH2 | 79-80 |

TABLE 5

| | Y | Ar | X | Melting Point (°C) |
|---|---|---|---|---|
| 65 | pyrazine-2-carbonyl | 6-chloropyridin-3-yl | NH | 172-174 |
| 66 | 4-(trifluoromethyl)pyridine-3-carbonyl | 6-chloropyridin-3-yl | NH | 137-139 |
| 67 | —COCH(CF3)2 | 6-chloropyridin-3-yl | S | 118-119 |
| 70 | bicyclo[2.2.1]hept-5-ene-2-carbonyl | 6-chloropyridin-3-yl | S | Oil |
| 71 | adamantane-1-carbonyl | 6-chloropyridin-3-yl | S | 138 |

TABLE 6

| Compound No. | Y | Ar | X | Melting Point (°C) |
|---|---|---|---|---|
| 72 | —COCH3 | 6-chloropyridin-3-yl | S | 108-110 |
| 73 | —COCH2Cl | 6-chloropyridin-3-yl | S | 111-112 |
| 74 | —COCHCl2 | 6-chloropyridin-3-yl | S | 124-126 |
| 75 | —COCH2Br | 6-chloropyridin-3-yl | S | 95-97 |
| 76 | —COCHF2 | 6-chloropyridin-3-yl | S | 61 |
| 77 | —COCClF2 | 6-chloropyridin-3-yl | S | 86-88 |
| 78 | —COCH2OCH3 | 6-chloropyridin-3-yl | S | 103-104 |
| 79 | —COCH2CN | 6-chloropyridin-3-yl | S | 122 |
| 80 | —COCH2OC6H5 | 6-chloropyridin-3-yl | S | 167 |
| 81 | —COCH2CH2OCH3 | 6-chloropyridin-3-yl | S | 56-57 |
| 82 | —COCH2NCS | 6-chloropyridin-3-yl | S | 147-149 |

TABLE 6-continued
| Compound No. | Y | Ar | X | Melting Point (°C.) |
|---|---|---|---|---|
| 83 | —COCH=CH2 | 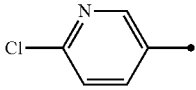 | S | 92-93 |
| 84 | —COCCl=CCl2 | 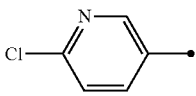 | S | 98-100 |
| 85 | —COCH2CH=CHCH3 | 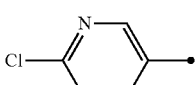 | S | 75-77 |
| 86 | COCH$_2$—C≡CCH$_3$ | 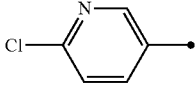 | S | 132-134 |
| 87 | —COCCH3(CF3)2 | 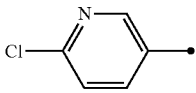 | S | 114-116 |
| 88 | —COCO2CH2CH3 | 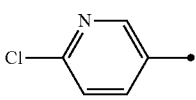 | S | 88-89 |
| 89 | —COCH2SCH3 | 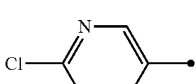 | S | Oil |
TABLE 7
| 90 | —COCH2CH2SCH3 | 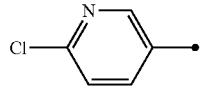 | S | 88-89 |
| 91 | —COCH2CH2SOSCH3 | 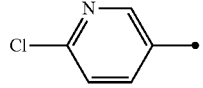 | S | 139-141 |
| 92 | 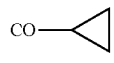 | 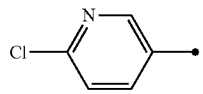 | S | 83-84 |
| 96 | 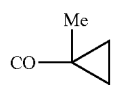 | 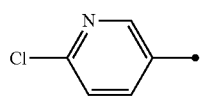 | S | 92-93 |
| 94 | 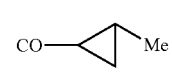 | 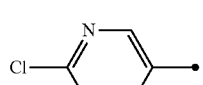 | S | 56-59 |
| 95 |  | 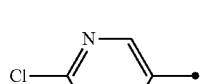 | S | 72-74 |
| 96 |  | 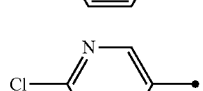 | S | 123-125 |
TABLE 7-continued
| 100 | 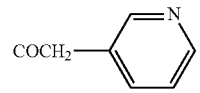 | 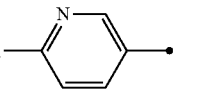 | S | 156-157 |
| 101 | 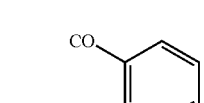 | 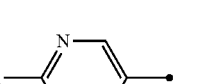 | S | 157-158 |
| 102 | 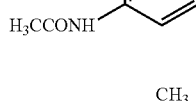 | 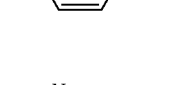 | S | 153-155 |
| 103 | 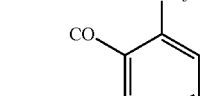 | 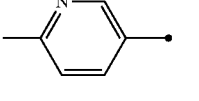 | S | 102-103 |
| 104 |  | 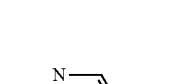 | S | 172-173 |

TABLE 7-continued
| | | | | |
|---|---|---|---|---|
| 106 | —CONHOCH3 | 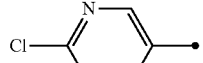 | S | 124-126 |
| 107 | —CONHOCH2CH3 | 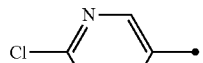 | S | 93-94 |
TABLE 8
| | | | | |
|---|---|---|---|---|
| 110 | 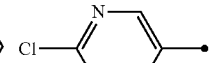 | 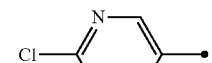 | S | |
| 111 | —CONHCH2CH2OCH3 | 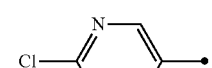 | S | 151-152 |
| 113 | —CO2CH2CH3 | 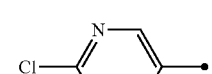 | S | 112-114 |
| 114 | —CO2CH2CH2F | 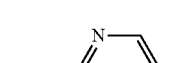 | S | 144 |
| 115 | —CO2CH2CHF2 | 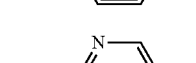 | S | 113 |
| 116 | —CO2CH2CF3 | 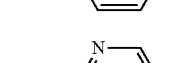 | S | 88-90 |
| 117 | —CO2CH2CCl3 | 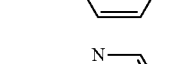 | S | 112-114 |
| 118 | —CO2CH2CH2OCH3 | 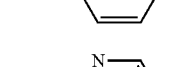 | S | 69-71 |
| 119 | —CO2CH2CH2SCH3 | 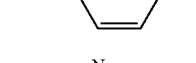 | S | 75-76 |
| 120 | —CO2CH2CH2Si(CH3)3 | 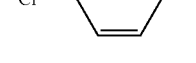 | S | 185-186 |
| 121 | —CO2CH2CH2OCH2CF3 | 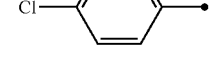 | S | 48 |
| 122 | —CO2CH2CH2CH2F | 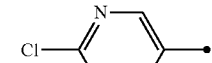 | S | 73 |
TABLE 8-continued
| | | | | |
|---|---|---|---|---|
| 123 | —CO2CH(CH2F)2 | 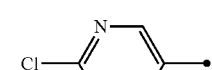 | S | 138-140 |
| 124 | —CO2CH(CF3)CH3 | 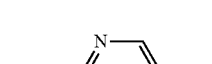 | S | 130-132 |
| 125 | —CO2CH(CF3)2 | 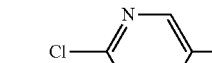 | S | 161-163 |
| 126 | —CO2CH2CH=CH2 | 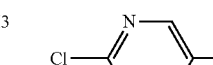 | S | 81-83 |
| 127 | —CO2CH2CCl=CCl2 | 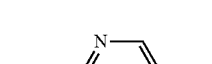 | S | 125-127 |
| 128 | —CO2(CH2)3CH3 | 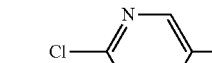 | S | 95-96 |
TABLE 9
| | | | | |
|---|---|---|---|---|
| 129 | —CO2CH2CH(CH3)2 | 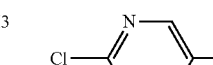 | S | 62-63 |
| 130 | —CO2CH(CH3)CH2CH3 | 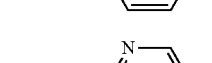 | S | 77-78 |
| 131 | —CO2C(CH3)3 | 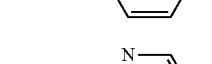 | S | 156 |
| 132 | —CO2(CH2)4F | 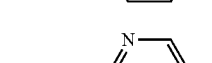 | S | 93-94 |
| 133 | —CO2(CH2)3CF3 | 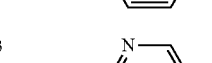 | S | 87-88 |
| 134 | —CO2CH2CF2CF2CF3 | 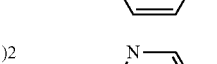 | S | 75 |
| 135 | —CO2CH2CH=C(CH3)2 | | S | 59-61 |
| 136 | —CO2(CH2)4CH3 | 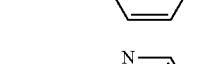 | S | 59-61 |

TABLE 9-continued

| # | R | Ar | | mp |
|---|---|---|---|---|
| 137 | —CO2(CH2)5CH3 | 6-chloropyridin-3-yl | S | 43 |
| 138 | —CO2CH2C(CH3)3 | 6-chloropyridin-3-yl | S | 162-163 |
| 139 | CO2CH2-cyclopropyl | 6-chloropyridin-3-yl | S | 117-118 |
| 140 | CO2CH2-(oxiranyl) | 6-chloropyridin-3-yl | S | 70-71 |
| 141 | CO2-cyclobutyl | 6-chloropyridin-3-yl | S | 123 |
| 142 | CO2-(oxetanyl) | 6-chloropyridin-3-yl | S | 124-125 |
| 143 | CO2-cyclopentyl | 6-chloropyridin-3-yl | S | 102-103 |
| 144 | CO2CH2-(tetrahydrofuran-3-yl) | 6-chloropyridin-3-yl | S | 103 |
| 145 | CO2CH2-(2,2-dimethyl-1,3-dioxolan-4-yl) | 6-chloropyridin-3-yl | S | Oil |
| 146 | CO2-(tetrahydropyran-4-yl) | 6-chloropyridin-3-yl | S | 101-102 |
| 147 | CO2CH2-(tetrahydropyran-2-yl) | 6-chloropyridin-3-yl | S | 101-102 |

TABLE 10

| # | R | Ar | | mp |
|---|---|---|---|---|
| 148 | CO2-(4-nitrophenyl) | 6-chloropyridin-3-yl | S | 167-168 |
| 149 | CO2CH2-(2-methoxyphenyl) | 6-chloropyridin-3-yl | S | 98-100 |
| 150 | CO2CH2-(pyridin-3-yl) | 6-chloropyridin-3-yl | S | 87-89 |
| 151 | CO2CH2-(pyridin-4-yl) | 6-chloropyridin-3-yl | S | Oil |
| 152 | CO2CH2-(furan-2-yl) | 6-chloropyridin-3-yl | S | 77-79 |
| 153 | CO2CH2-(furan-3-yl) | 6-chloropyridin-3-yl | S | 94-96 |
| 154 | CO2CH2-(thiophen-2-yl) | 6-chloropyridin-3-yl | S | 50-52 |
| 155 | CO2CH2-(thiophen-3-yl) | 6-chloropyridin-3-yl | S | 90-92 |

TABLE 10-continued

| # | R | Aryl | X | mp (°C) |
|---|---|---|---|---|
| 156 | 3-pyridyl-CO2- | 6-chloropyridin-3-yl | S | 104-105 |
| 158 | —CO2CH3 | 2-chlorothiazol-5-yl | S | 120-121 |
| 159 | —CO2CH2CH3 | 2-chlorothiazol-5-yl | S | 131-133 |
| 160 | —CO2CH(CH3)2 | 2-chlorothiazol-5-yl | S | 102-105 |
| 161 | —CO2(CH2)3CH3 | 2-chlorothiazol-5-yl | S | 78-79 |
| 162 | (tetrahydrofuran-3-yl)-CO2- | 2-chlorothiazol-5-yl | S | Oil |
| 163 | PhO-CO2- (phenyl-CO2-) | 2-chlorothiazol-5-yl | S | 127-129 |
| 167 | —CO2CH(CH3)2 | 6-chloropyridin-3-yl | CH2 | Oil |
| 168 | —COCF3 | 6-chloropyridin-3-yl | CH2 | 58-59 |
| 169 | —CO2CH3 | 6-chloropyridin-3-yl | NH | 164-166 |

TABLE 11

| # | R | Aryl | X | mp (°C) |
|---|---|---|---|---|
| 170 | —CO2CH3 | 6-chloropyridin-3-yl | NCH3 | 82-83 |
| 171 | —CO2CH2C≡CH | 6-chloropyridin-3-yl | S | 116-118 |
| 172 | CO2CH2—CH(OCH2CH2)6—O—CH2 (cyclic) | 6-chloropyridin-3-yl | S | Oil |
| 173 | —CO2CH2CH2CH=CH2 | 6-chloropyridin-3-yl | S | 88-90 |

TABLE 12

| Compound No. | IR (KBr, ν, cm⁻¹) | NMR (DMSO-d₆, δ, ppm) |
|---|---|---|
| 1 | 1656, 1542, 1462, 1422 | 3.29(2H, t), 3.75(2H, t), 4.86(2H, s), 7.35(1H, d), 7.68(1H, dd), 8.35 (1H, d) |
| 2 | 1638, 1536, 1463, 1410 | 3.18(2H, t), 3.68(2H, q), 3.63(2H, t), 4.82(2H, s), 7.34(1H, d), 7.66(1H, dd), 8.34 (1H, d) |
| 3 | 1630, 1602, 1527, 1462, 1402 | 1.23(9H, s), 3.1 (2H, dd), 3.74 (2H, dd), 4.82(2H, s), 7.32(1H, d), 7.67 (1H, dd), 8.38 (1H, d) |
| 4 | 1640, 1534, 1426, 1402 | 1.70(3H, s), 3.22(2H, t), 3.67(2H, t), 4.84(2H, s), 7.34(1H, d), 7.65(1H, d), 8.33(1H d) |
| 5 | 1657, 1536, 1460, 1402, 838 | 3.27(2H, dd), 3.74(2H, dd), 4.87(2H, s), 7.34(2H, d), 7.78(1H, dd), 8.40(2H, d) |
| 6 | 1615, 1522, 1455, 1401 | 3.19(2H, dd), 3.62(2H, dd), 4.98(2H, s), 7.32(1H, d), 7.43(2H, m), 7.50(1H, m), 7.72(1H, dd), 8.26(2H, m), 8.40(1H, d) |
| 7 | 1618, 1527, 1457, 1402 | 3.20(2H, dd), 3.63(2H, dd), 4.97(2H, s), 7.33(1H, d), 7.39(2H, d), 7.68 (1H, dd), 8.19(2H, d), 8.39(1H, d) |
| 8 | 1620, 1531, 1457, 1408 | 2.40(3H, s), 3.18(2H, t), 3.60(2H, t), 4.97(2H, s), 7.22(2H, d), 7.32(1H, d), 7.73 (1H, dd), 8.16(2H, d), 8.39(1H, d) |
| 9 | 1630, 1528, 1460, 1406 | 1.25-2.00(10H. m), 2.39(1H, m), 3.10(2H, dd), 3.53(2H, dd), 4.82(2H, s), 7.32(2H, d), 7.64(1H, dd), 8.35(2H, d) |
| 10 | 1726, 1631, 1531, 1397 | 3.08(2H, dd), 3.51(2H, dd), 3.78(2H, s), 4.71(2H, s), 7.18(1H, d), 7.21-7.32(5H, m), 7.38(1H, dd), 8.24(1H, d) |
| 11 | 1728, 1626, 1614, 1589, 1529, 1457 | 3.24(2H, dd), 3.68(2H, dd)5.03(2H, s), 734(1H, d), 7.58((1H, m), 7.74(1H, dd), 7.78-7.81(2H, m), 7.93-8.18(1H, m), 8.42(1H, d), 8.99(1H, d), 9.73(1H, d) |
| 12 | 1587, 1551, 1506, 1459, 1425, 1402 | 3.15(2H, dd), 3.57(2H, dd), 4.94(2H, s), 7.17(1H, m), 7.30(1H, d), 7.42(1H, d), 7.73(1H, dd), 8.04(1H, d), 8.41(1H, d), 10.8(1H, bs) |
| 13 | 1625, 1524, 1460, 1402, 1282 | 3.22(2H, t), 3.66(2H, t), 4.98(2H, s), 7.32(1H, d), 7.36(1H, m), 7.71(1H, bd), 8.39(1H, bs), 8.47(1H, d), 8.72(1H, m), 8.48(1H, s) |
| 14 | 1717, 1680, 1637, 1530, 1460, 1410 | 3.25(2H, dd), 3.68(2H, dd), 5.00(2H, s), 7.33(1H, d), 7.75(1H, dd), 8.42(1H, d), 8.68(1H, d), 8.74(1H, d), 9.49(1H, d) |

TABLE 13

| | | |
|---|---|---|
| 15 | 1627, 1528, 1461, 1405, 1352, 1297 | 3.23(2H, dd), 3.67(2H, dd), 4.96(2H, s), 7.32(1H, d), 7.39(1H, d), 7.67(1H, bd), 8.37(1H, bs), 8.40(1H, d), 9.22(1H, s) |
| 16 | 1720, 1639, 1523, 1430, 1407, 1384 | 3.23(2H, dd), 3.73(2H, dd), 4.97(2H, s), 7.34(1H, d), 7.75(1H, dd), 8.42 (1H, d), 8.69(1H, s), 9.34(1H, s) |
| 17 | 1727, 1622, 1530, 1458, 1400 | 3.26(2H, dd), 3.70(2H, dd), 4.98(2H, s), 7.37(1H, d), 7.65(1H, dd), 7.96 (2H, s), 8.36(1H, d) |
| 18 | 1727, 1626, 1534, 1461, 1406 | 3.30(2H, dd), 3.82(2H, dd), 5.05(2H, s), 7.52(1H, d), 7.87(1H, dd), 8.19(1H, m), 8.48(1H, d), 9.44(1H, m), 9.74(1H, d) |
| 19 | 1634, 1561, 1531, 1460, 1412 | 3.22(2H, dd), 3.69(2H, dd), 4.95(2H, s), 7.35(1H, d), 7.44(1H, d), 7.77 (1H, dd), 8.01(1H, d), 8.17(1H, d), 8.40(1H, d) |
| 20 | 1725, 1624, 1531, 1462, 1402 | 3.24(2H, dd), 3.67(2H, dd), 4.98(2H, s), 7.35(1H, d), 7.68 (1H, bd), 8.38 (1H, bs), 8.59 (1H, bs), 8.77(1H, bs), 9.35(1H, bs) |
| 21 | 1720, 1630, 1532, 1461, 1402 | 3.24(2H, dd), 3.65(2H, dd), 4.89(2H, s), 7.34(1H, d), 7.59(1H, dd), 7.62(1H, d), 8.34(1H, d), 8.83(1H, d), 9.18(1H, d) |
| 22 | 1629, 1524, 1458, 1402 | 3.24(2H, dd), 3.68(2H, dd), 4.97(2H, s), 7.34(1H, d), 7.67(1H, dd), 8.38(1H, d), 8.50(1H, d), 9.09(1H, d) |
| 23 | 1727, 1634, 1566, 1527, 1459, 1402 | 3.24(2H, dd), 3.68(2H, dd), 4.92(2H, s), 7.31-7.35(2H, m), 7.56(1H, dd), 8.25(1H, d), 8.36(1H, d) |
| 24 | 1648, 1622, 1529, 1496, 1404 | 3.25(2H, t), 3.68(2H, t), 4.85(2H, s), 7.35(2H, d), 7.68(1H, dd), 8.34 (2H, d) |
| 28 | 1655, 1611, 1558, 1380, 1312 | 3.10(2H, t), 3.54(2H, t), 4.75(2H, s), 7.33(2H, d), 7.68(1H, d), 8.35(1H d) |
| 29 | 1620, 1611, 1578, 1525, 1459, 1435 | 2.87(3H, d), 3.09(2H, t), 3.48(2H, t), 4.70(2H, s), 5.23(1H, bs), 7.30(2H, d), 7.60(1H, dd), 8.31(1H, d), |
| 30 | 1742, 1610, 1578, 1531, 1460, 1290 | 1.22(3H, t), 3.10(2H, m), 3.56(2H, m), 3.82(2H, s), 4.10(2H, q), 4.74 (2H, s), 7.20 (1 H, bs), 7.40 (1H, m), 7.78(1H, m), 8.41(1H, bs) |
| 31 | 1726, 1700, 1655, 1552, 1475, 1459 | 3.18(2H, m), 3.71(2H, m), 4.60(2H, s), 4.78(2H, s), 7.46(1H, bs), 7.91(1H, bs), 8.51(1H, bs), 10.44(1H, bs) |
| 32 | 1718, 1549, 1497, 1483, 1469, 1438 | 3.17(2H, dd), 3.61(2H, dd), 4.79(2H, s), 7.34(1H, m), 7.44-7.46(2H, m), 7.53(1H, m), 7.68(1H, m), 7.83(2H, m), 8.35(1H, bs), 8.65(1H, bs) |
| 33 | 1661, 1628, 1551, 1449, 1423, 1400 | 3.07(2H, m), 3.58(2H, m), 4.59(2H, s), 7.18-7.58(5H, m), 7.70(1H, m), 7.85(1H, m), 8.36(1H, bs) |

TABLE 14

| | | |
|---|---|---|
| 34 | 1632, 1615, 1580, 1531, 1457, 1280 | 1.18(6H, d), 3.08(2H, t), 3.47(2H, t), 4.71(2H, s), 5.14(1H, bs), 7.30(2H, d), 7.601H, d), 8.32(1H, d) |
| 35 | 1634, 1557, 1457, 1418, 1273, 1233 | 3.10(2H, dd), 3.52(2H, dd), 3.63-3.72(8H, m), 4.75(2H, s), 7.32(1H, d), 7.61(1H, dd), 8.33(1H, d) |

TABLE 14-continued

| | | |
|---|---|---|
| 36 | 1648, 1562, 1513, 1466, 1437, 1311 | 3.13(2H, dd), 3.50(2H, dd), 4.76(2H, s), 5.21(1H, bs), 7.03(1H, m), 7.20 (1H, bs), 7.26-7.40(3H, m), 7.50-7.65(3H, m), 8.32(1H, bs) |
| 37 | 1684, 1628, 1562, 1508, 1460, 1385 | 1.1-2.1(10H, m), 3.09(2H, m), 3.47(2H, m), 3.66(1H, m), 4.73(2H, s), 5.19(2H, bs), 7.30(1H, m), 7.62(1Hm), 8.34(1H, bs) |
| 42 | 1662, 1555, 1459, 1440, 1264 | 3.18(H, dd), 3.60(2H, dd), 3.79(3H, s), 4.81(2H, s), 7.32(1H, d), 7.67(1H, dd), 8.31(1H, d) |
| 43 | 1564, 1543, 1463, 1429, 1415, 1260 | 0.97(3H, t), 1.74(2H, tq), 3.15(2H, t), 3.56(2H, t), 4.12(2H, t), 4.81(2H, s), 7.32(1H, d), 7.65(1H, dd), 8.31(2H, d) |
| 44 | 1652, 1545, 1465, 1415, 1262, 1239 | 1.32(6H, d), 3.14(2H, t), 3.54(2H, t), 4.82(2H, s), 5.01(1H, sep), 7.35(1H, d), 7.62(1H, dd), 8.31(1H, d) |
| 45 | 1657, 1563, 1434, 1265 | 3.18(2H, dd), 3.60(2H, dd), 3.75(2H, t), 4.41(2H, t,), 4.82(2H, s), 7.32(1H, bs), 7.65(1H, bd), 8.32(1 H, bs) |
| 46 | 1657, 1572, 1558, 1460, 1436, 1420, | 3.16(2H, dd), 3.39(3H, s), 3.67(2H, dd), 3.67(2H, t,), 4.32(2H, t), 4.81(2H, s), 7.32(1H, d), 7.65(41H, dd), 8.30(1H, d) |
| 47 | 1686, 1664, 1541, 1470, 1455, 1428 | 3.15(2H, t), 3.55(2H, t), 4.78(2H, s), 5.20(2H, s), 7.26-7.43(6H, m), 7.63(1H, dd), 8.29(1H, d) |
| 48 | 1692, 1551, 1214 | 3.20(2H, t), 3.64(2H, t), 4.83(2H, s), 7.14(2H, d), 7.31-7.36(3H, m), 7.66(1H, dd), 8.35(1H, d) |
| 49 | 1684, 1548, 1420, 1213, 1141 | 3.20(2H, dd), 3.64(2H, dd), 4.80(2H, s), 7.16(1H, m), 7.24-7.34(3H, m), 7.42(1H, m), 7.65(1H, m), 8.31(1H, m) |
| 50 | 1730, 1717, 1551, 1420, 1221 | 2.53(2H, m), 2.76(4H, s), 3.85(2H, m), 4.81(2H, s), 7.53(1H, d), 7.78(1H, bd), 8.39(1H, bs) |
| 51 | 1637, 1570, 1460, 1445, 1423, 1265 | 3.19(2H, dd), 3.62(2H, dd), 4.84(2H, s), 7.19-7.25(3H, m), 7.34-7.40(1H, m), 7.64(1H, dd), 8.33(1H, d) |
| 52 | 1656, 1552, 1464, 1446, 1426, 1266 | 0.88(3H, t), 1.30-1.40(6H, m), 1.68-1.72(2H, m), 3.15(2H, t,), 3.56(2H, t), 4.16 (2H, t), 4.81(2H, s), 7.32 (1H, d), 7.64(1H, dd), 8.31(1H, t) |
| 53 | 1664, 1546, 1271, 1232, 1209, 1157 | 3.25(2H, dd), 3.74(2H, dd), 4.80(2H, s), 7.29-7.35(2H, m), 7.46-7.55(2H, m), 7.61-7.70(2H, m), 7.84-7.88(3H, m), 8.37(1H, bs) |

TABLE 15

| | | |
|---|---|---|
| 56 | 1656, 1535, 1524, 1408 | 3.29(2H, t), 3.79 (2H, t), 4.96(2H, s), 7.53(1H, s) |
| 57 | 1617, 1522, 1445, 1407 | 3.20(2H, dd), 3.68(2H, dd), 5.02(2H, s), 7.40-7.54(3H, m), 7.51(1H, s), 8.32(2H, m) |
| 58 | 1617, 1536, 1401, 1380 | 3.25(2H, dd), 3.64(2H, t), 4.85(2H, s), 7.34(1H, d), 7.69(1H, dd), 8.33(1H, d), 8.97(1H, s) |
| 59 | 1687, 1639, 1593, 1459, 1386 | 2.17(2H, m), 3.06(4H, m), 3.60(2H, t,), 4.82(2H, s), 7.37(1H, d), 7.72(1H, dd), 8.30(1H, s), 8.35(1H, d) |
| 60 | 1730, 1690, 1567, 1462, 1388, 1371, 1286 | 3.39(2H, t), 3.69(2H, t), 4.58(2H, s), 7.33(1H, d), 7.67(1H, d), 8.32(1H, s), 8.58(1H, s), 8.61(1H, bs) |
| 61 | 1620, 1520, 1411, 1383 | 3.25(2H, t), 3.69(2H, dd), 4.89(2H, s), 7.48(1H, s), 8.97(1H, s) |
| 62 | 1684, 1600, 1416, 1352 | 2.18(2H, m), 3.06(2H m), 3.67(2H, t), 5.07 2H, s), 7.63(1H, s), 8.36(1H, s) |
| 63 | 1729, 1650, 1555, 1479, 1469 | 2.14(2H, m), 3.29(2H, t), 3.71(2H, t), 4.84(2H, s), 7.33(1H, d), 7.73(1H, dd), 8.39(1H, d), 8.66(1H, d), 8.71(1H, bs), 9.47(1H, s) |
| 64 | 1637, 1560, 1489, 1460, 1318 | 3.14(2H, m), 3.27(2H, t), 3.44(2H, t), 4.74(2H, s), 7.32(1H, d), 7.56(1H, d), 7.62(1H, dd), 8.32(1H, d), 8.79(1H, d), 9.11(1H, s) |
| 65 | 1627, 1606, 1576, 1551, 1459 | 3.47(2H, t), 3.78(2H, dd), 4.72(2H, s), 7.33(1H, d), 7.72(1H, bd), 8.38(1H, bs), 8.64(1H, d), 8.65(1H, bs), 8.71(1H, d), 8.91(1H, bs), 9.52(1H, s) |
| 66 | 1611, 1567, 1463, 1380, 1347 | 3.45(2H, t), 3.76(2H, t), 4.62(2H, s), 7.33(1H, d), 7.56(1H, d), 7.64(1H, dd), 8.32(1H, d), 8.71(1H, bs), 8.77(1H, d), 9.12(1H, s) |
| 67 | 1639, 1531, 1412, 1305 | 3.23(2H, t), 3.62(2H, t), 4.04(1H, m) 4.83(2H, s), 7.34 (1H, d), 7.65(1H, dd), 8.33 (1H, d) |
| 70 | 1632, 1525, 1463, 1401 | 1.31-2.05(4H, m), 2.90(1H, m), 3.08-3.28(3H, m), 3.28(1H, m), 3.54(2H, t), 4.82(2H, s), 5.90(1H, m), 6.15(1H, m), 7.33(1H, m), 7.66(1H, m), 8.36 (1H, m) |
| 71 | 2903, 2848, 1637, 1525, 1455 | 1.68-2.04(15H, m), 3.11(2H, dd), 3.54(2H, dd), 4.83(2H, s), 7.32(1H, d), 7.67(1H, dd), 8.37(1H, d) |

TABLE 16

| Compound No. | IR (KBr, ν, cm⁻¹) | NMR (DMSO-d₆, δ, ppm) |
|---|---|---|
| 72 | 1627, 1525, 1396, 1270 | 2.23(3H, t), 3.11(2H, t), 3.51(2H, t), 4.79(2H, s), 7.30(1H, d), 7.63(1H, dd), 8.32 (1H, d) |
| 73 | 1644, 1533, 1419, 793 | 3.18(2H, t), 3.64(2H, t), 4.21(2H, s), 4.83(2H, s), 7.33(1H, d), 7.69(1H, bd), 8.35 (1H, bs) |
| 74 | 1646, 1534, 1427, 818 | 3.23(2H, dd), 3.70(2H, dd), 4.86(2H, s), 6.06(1H, s), 7.34(1H, d), 7.76(1H, dd), 8.39 (1H, d) |
| 75 | 1640, 1532, 1416, 1290, 1250, 1183 | 3.17(2H, t), 3.63(2H, t), 4.02(2H, s), 4.83(2H, s), 7.34(2H, d), 7.32(1H, d), 7.72(1H, dd), 8.36(1H d) |

TABLE 16-continued

| Compound No. | IR (KBr, ν, cm$^{-1}$) | NMR (DMSO-d$_6$, δ, ppm) |
|---|---|---|
| 76 | 1654, 1548, 1431, 1241, 1109 | 3.24(2H, t), 3.68(2H, t), 4.87(2H, s), 5.94(1H, t), 7.35(2H, d), 7.68(1H, bd), 8.34(1H, bs) |
| 77 | 1660, 1541, 1418, 1141, 1112, 959 | 3.28(2H, t), 3.75(2H, t), 4.86(2H, s), 7.34(2H, d), 7.73(1H, dd), 8.38 (2H, d) |
| 78 | 1653, 1538, 1456, 1423, 1238 | 3.15(2H, t), 3.48(3H, s), 3.67(2H, t), 3.78(2H, s), 4.16(2H, s), 4.80(2H, s), 7.33(1H, d), 7.63(1H, d), 8.24(1H, s) |
| 79 | 2361, 1642, 1529, 1409, 1389 | 3.21(2H, t), 3.52(2H, s), 3.67(2H, t), 4.85(2H, s), 7.35(1H, d), 7.39(1H, bd), 7.67 (1H, bs), 8.37(1H, bs) |
| 80 | 1662, 1542, 1417, 1239, 754 | 3.13(2H, t), 3.56(2H, t), 4.73(2H, s), 4.74(2H, s), 6.90-6.95(3H, m), 7.22-7.27(3H, m), 7.45(1H, dd), 8.27(1H, d) |
| 81 | 1726, 1635, 1531, 1460, 1406, 1289 | 2.75(2H, t), 3.12(2H, t), 3.35(3H, s), 3.56(2H, t), 3.74(2H, t), 4.82(2H, s), 7.31(1H, m), 7.68(1H, dd), 8.34(1H, d) |
| 82 | 2152, 1615, 1530, 1429, 1191, 1129 | 3.21(2H, t), 3.65(2H, t), 3.95(2H, s), 4.86(2H, s), 735(1H, d), 7.67(1H, dd), 8.35(1H, d) |
| 83 | 1640, 1592, 1537, 1405, 1241 | 3.16(2H, t), 3.59(2H, t), 4.87(2H, s), 5.79(1H, dd), 6.40(1H, dd), 6.47(1H, dd), 7.33(1H, d), 7.68(1H, bd), 8.37(1H, bs) |
| 84 | 1626, 1528, 1462, 1410, 1386, 1242 | 3.22(2H, t), 3.67(2H, t), 4.86(2H, s), 7.34(1H, d), 7.68(1H, dd), 8.38(1H, d) |
| 85 | 1634, 1530, 1464, 1437, 1403, 1233 | 1.69(3H, d), 3.11(2H, t), 3.19(2H, m)3.54(2H, t), 4.80(2H, s), 5.56(1H, m), 5.67(1H, m), 7.31(1H, d), 7.67((1H, dd), 8.34(1H, d) |
| 86 | 2235, 1598, 1530, 1413, 1279, 1248 | 2.01(3H, s), 3.17(2H, t), 3.62(2H, t), 4.86(2H, s)7.34(1H, d), 7.69(1H, dd), 8.35(1H, d) |

TABLE 17

| | | |
|---|---|---|
| 87 | 1640, 1543, 1462, 1402 | 1.70(3H, s), 3.22(2H, t), 3.67(2H, t), 4.84(2H, s), 7.34(1H, d), 7.65(1H, dd), 8.33(1H, d) |
| 88 | 1733, 1634, 1540, 1460, 1411, 1390 | 1.38(3H, t), 3.22(2H, t), 3.69(2H, t), 4.33(2H, q), 4.89(2H, s), 7.34(1H, d), 7.77(1H, dd), 8.37(1H, d) |
| 89 | 1628, 1530, 1460, 1406, 1281, 1246 | 2.19(3H, s), 3.16(2H, t), 3.36(2H, s), 3.60(2H, t), 4.83(2H, s), 7.32(1H, d), 7.74(1H, dd), 8.36(1H, d) |
| 90 | 1636, 1533, 1401, 1243, 1130, 1104 | 2.13(3H, s), 2.80(2H, m), 2.83(2H, m), 3.13(2H, t), 3.55(2H, t), 4.82(2H, s), 7.32(1H, d), 7.65(1H, dd), 8.34(1H, d) |
| 91 | 1651, 1557, 1456, 1442, 1289, 1237 | 3.01(3H, s), 3.21(2H, t), 3.39(2H, t), 3.61(2H, t), 4.57(2H, t), 4.78(2H, s), 7.33(1H, d), 7.63(1H, dd), 8.31(1H, d) |
| 92 | 1619, 1535, 1458, 1405 | 0.85(2H, m), 1.05(2H, m), 1.84(1H, m), 3.11(2H, t), 3.54(2H, t), 4.81 (2H, s), 7.33 (1H, d), 7.65(1H, dd), 8.34(1H, d) |
| 93 | 1620, 1532, 1460, 1407, 1125 | 0.70(2H, m), 1.30(2H, m), 1.35(3H, s), 3.10(2H, t), 3.53(2H, t), 4.75 (2H, s), 7.32(1H, d) , 7.65(1H, dd), 8.32(1H, d) |
| 94 | 1622, 1532, 1460, 1407 | 0.68(1H, m), 1.12(3H, d), 1.24(1H, m), 1.45(1H, m), 1.58(1H, m), 3.09 (2H, t), 3.52(2H, t), 4.78(1H, d), 4.82(1H, d), 7.33(1H, d), 7.64(1H, dd), 8.34(1H, d) |
| 95 | 1629, 1529, 1411, 1238, 1222 | 2.14(1H, m), 2.28(1H, m), 3.15(2H, t), 3.24(1H, m), 3.56(2H, t), 3.84(1H, m), 3.89(1H, m), 3.98(1H, m), 4.02(1H, m), 4.82(2H, s), 7.34(1H, d), 7.64(1H, dd), 8.34(1H, d) |
| 96 | 1627, 1531, 1468, 1417, 1292, 1098 | 3.18(2H, t), 3.62(2H, t), 4.90(2H, s), 6.50(1H,dd), 7.21(1H, d), 7.32(1H, d), 7.58(1H, bs), 7.40(1H, dd), 8.40(1H, d) |
| 100 | 1628, 1537, 1458, 1396, 1236, 1189 | 3.11(2H, t), 3.54(2H, t), 3.77(3H, s), 4.73(2H, s), 7.23(2H, m), 7.43(1H, m), 7.64(1H, bd), 8.26(1H, bs), 8.47(1H, bs), 8.55(1H, bs) |
| 101 | 1682, 1618, 1592, 1518, 1505, 1335 | 2.25(3H, s), 3.22(2H, t), 3.65(2H, t), 4.96(2H,s), 7.05(1H, m), 7.33(1H, d), 7.49(1H, m), 7.69(1H, m), 8.38(1H, d), 8.43(1H, m), 8.70(1Hm), 12.0(1H, bs) |
| 102 | 1683, 1609, 1532, 1506, 1460, 1281 | 2.22(3H, s), 2.29(3H, s), 3.19(2H, t), 3.62(2H, t), 4.92(2H, s), 7.13(1H, t), 7.32(1H, d), 7.36(1H, d), 7.69(1H, m), 8.09(1H, d), 8.36(1H, bs), 10.1(1H, bs) |

TABLE 18

| | | |
|---|---|---|
| 103 | 1626, 15361460, 1427, 1371, 1129 | 1.69(1H, m), 2.15(1H, m), 2.66(1H, m), 3.15(2H, m), 3.57(2H, m), 4.73(1H, d), 4.91(1H, d), 7.34(1H, d), 7.64(1H, dd), 8.34(1H, d) |
| 104 | 2959, 2930, 1729, 1536, 1287, 1131 | 3.17(2H, t), 3.60(2H, t), 4.68(2H, s), 4.77(2H, s), 6.98(1H, s), 7.08(1H, s), 7.31(1H, d), 7.42(1H, dd), 7.53(1H, s), 8.26(1H, d) |
| 106 | 3222, 1620, 1568, 1439, 1238, 1100 | 3.14(2H, t), 3.54(2H, t), 3.79(3H, s), 4.71(2H, s), 7.32(1H, d), 7.61(1H, dd), 7.81(1H, bs), 8.32(1H, d) |
| 107 | 3435, 1632, 1565, 1272, 1109, 1085 | 1.27(3H, t), 3.13(2H, t), 3.54(2H, t), 3.99(2H, q), 4.71(2H, s), 7.31(1H, d), 7.63(1H, bs), 7.85(1H, bs), 8.31(1H, d) |
| 110 | 3298, 1608, 1570, 1508, 1436, 1239 | 3.10(2H, t), 3.48(2H, t), 4.60(2H, d), 4.74(2H, s), 6.24(1H, bs), 7.16(1H, m), 7.30-7.35'2H, m), 7.65(1H, m), 8.32(1H, bs), 8.54(1H, bd) |
| 111 | 3306, 1607, 1578, 1531, 1459, 1279 | 3.08(2H, t), 3.37(3H, s), 3.50(6H, m), 4.71(2H, s), 5.58(1H, bs), 7.31(1H, d), 7.62(1H, dd), 8.31(1H, d) |

TABLE 18-continued

| | | |
|---|---|---|
| 113 | 1664, 1548, 1460, 1416, 1264, 1240 | 1.34(3H, t), 3.16(2H, t), 3.57(2H, t), 4.22(2H, q), 4.81(2H, s), 7.32(1H, d), 7.65(1H, dd), 8.31(1H, d) |
| 114 | 1641, 1557, 1405, 1322, 1286, 1143 | 3.18(2H, t), 3.59(2H, t), 4.41(2H, dt), 4.67(2H, dt), 4.82(2H, s), 7.33(1H, d), 7.65(1H, dd), 8.32(1H, d) |
| 116 | 1662, 1551, 1462, 1428, 1388, 1267 | 3.20(2H, t), 3.63(2H, t), 4.35(2H, td), 4.81(2H, s), 6.02(1H, tt), 7.33(1H, d), 7.64(1H, bd), 8.32(1H, bs) |
| 116 | 1678, 1547, 1459, 1291, 1237, 1141 | 3.21(2H, t), 3.63(2H, t), 4.55(2H, q), 4.82(2H, s), 7.34(1H, d), 7.66(1H, bd), 8.33(1H, bs) |
| 117 | 1668, 1536, 1460, 1443, 1429, 1231 | 3.21(2H, t), 3.63(2H, t), 4.55(2H, q), 4.85(2H, s), 7.34(1H, d), 7.68(1H, dd), 8.33(1H, d) |
| 118 | 1657, 1572, 1558, 1460, 1436, 1260 | 3.16(2H, dd), 3.39(3H, s), 3.57(2H, dd), 3.67(2H, t), 4.32(2H, t), 4.81(2H, s), 7.32(1H, d), 7.65(1H, dd), 8.30(1H, d) |
| 119 | 1660, 1551, 1459, 1435, 1264, 1240 | 2.17(3H, s), 2.81(2H, t), 3.17(2H, t), 3.39(3H, s), 3.58(2H, t), 4.32(2H, t), 4.81(2H, s), 7.32(1H, d), 7.65(1H, dd), 8.31(1H, d) |

TABLE 19

| | | |
|---|---|---|
| 120 | 2923, 2582, 1742, 1663, 1655, 1263 | 0.05(9H, s), 1.05(2H, t), 3.11(2H, t), 3.52(2H, t), 4.21(2H, t), 4.76(2H, s), 7.26(1H, d), 7.61(1H, bd), 8.26(1H, bs) |
| 121 | 1667, 1553, 1459, 1421, 1265, 1240 | 3.18(2H, t), 3.58(2H, t), 3.91(4H, overlap), 4.34(2H, t), 4.81(2H, s), 7.32 (1H, d), 7.66(1H, bd), 8.31(1H, bs) |
| 122 | 1657, 1543, 1465, 1429, 1414, 1260 | 2.10(2H, dtt), 3.17(2H, dd), 3.59(2H, dd), 4.29(2H, t), 4.57(2H, dtt), 4.81 (2H, s), 7.32(1H, d), 7.65(1H, dd), 8.31(1H, d) |
| 123 | 1654, 1558, 1542, 1457, 1419, 1260 | 3.17(2H, dd), 3.59(2H, dd), 4.61(2H, bs), 4.71(2H, bs), 4.81(2H, s), 5.20(1H, m), 7.32 (1H, d), 7.64(1H, bd), 8.31(1H, bs) |
| 124 | 1668, 1543, 1466, 1428, 1414, 1235 | 1.46(1H, d), 3.19(2H, t), 3.61(2H, t), 4.80(1H, d), 4.84(1H, d), 5.31(1H, m), 7.33(1H, d), 7.65(1H, bd), 8.32(1H, bs) |
| 125 | 1698, 1546, 1552, 1428, 1348, 1198 | 3.25(2H, dd), 3.68(2H, dd), 4.84(2H, s), 5.31(1H, m), 7.36(1H, d), 7.66 (1H, bd), 8.33(1H, bs) |
| 126 | 1655, 1545, 1465, 1431, 1415, 1210 | 3.17(2H, t), 3.58(2H, t), 4.67(2H, dt), 4.81(2H, s), 5.25(1H, dd), 5.37(1H, ddd), 6.02(1H, m), 7.32 (1H, d), 7.65(1H, dd), 8.31 (1H, d) |
| 127 | 1660, 1543, 1460, 1442, 1416, 1204 | 3.19(2H, t), 3.61(2H, t), 4.83(2H, s), 5.03(2H, s), 7.33(1H, d), 7.65(1H, dd), 8.31(1H, d) |
| 128 | 1659, 1560, 1456, 1435, 1389, 1157 | 0.94(3H, t), 1.41(2H, m), 1.70(2H, m), 3.15(2H, dd), 3.56(2H, dd), 4.17(2H, t), 4.81(2H, s), 7.32(1H, d), 7.65(1H, bd), 8.31(1H, bs) |
| 129 | 1657, 1550, 1462, 1419, 1264, 1146 | 0.96(6H, d), 3.15(2H, t), 3.56(2H, t), 3.95(2H, d), 4.82(2H, s), 7.32(1H, d), 7.65(1H, dd), 8.31(1H, d) |
| 130 | 1653, 1542, 1464, 1428, 1237, 1144 | 0.94(3H, t), 1.29(2H, d), 1.56-1.78(2H, m), 3.15(2H, t), 3.54(2H, t,), 4.78-4.86(1H, m), 4.82(2H, s), 7.32(1H, d), 7.63(1H, dd), 8.31(1H, d) |
| 131 | 1653, 1560, 1464, 1419, 1280, 1105 | 1.54(9H, s), 3.15(2H, t), 3.51(2H, t), 4.81(2H, s), 7.32(1H, d), 7.63(1H, bd), 8.31(1H, bs) |
| 132 | 1660, 1559, 1456, 1435, 1389, 1155 | 1.85(4H, m), 3.17(2H, t), 3.58(2H, d), 4.21(2H, m), 4.47(2H, bd), 4.82(2H, s), 7.32(1H, d), 7.65(1H, bd), 8.32(1H, bs) |
| 133 | 1662, 1552, 1459, 1422, 1254, 1148 | 1.98(2H, m), 2.23(2H, m), 3.18(2H, t), 3.59(2H, t), 4.23(2H, t), 4.84(2H, s), 7.33(1H, d), 7.65(1H, dd), 8.32(1H, d) |
| 134 | 1680, 1552, 1459, 1232, 1148, 1103 | 3.21(2H, t), 3.64(2H, t), 4.68(2H, m), 4.82(2H, s), 7.33(1H, d), 7.67(1H, bd), 8.33(1H, bs) |
| 135 | 1660, 1571, 1557, 1458, 1260, 1102 | 1.73(3H, s), 1.75(3H, t), 3.16(2H, t), 3.56(2H, t), 4.67(2H, d), 4.81(2H, s), 5.44(1H, m), 7.32(1H, d), 7.65(1H, dd), 8.30(1H, d) |

TABLE 20

| | | |
|---|---|---|
| 136 | 1660, 1561, 1456, 1436, 1330, 1155 | 0.90(3H, t), 1.36(4H, m), 1.72(2H, m), 3.15(2H, dd), 3.56(2H, dd), 4.16(2H, t), 4.81(2H, s), 7.32(1H, d), 7.64(1H, dd), 8.31(1H, d) |
| 137 | 1656, 1552, 1464, 1426, 1266, 1234 | 0.88(3H, t), 1.30-1.40(6H, m), 1.68-1.72(2H, m), 3.15(2H, t), 3.56(2H, t), 4.16(2H, t), 4.81(2H, s), 7.32(1H, d), 7.64(1H, dd), 8.31(1H, d) |
| 138 | 1661, 1546, 1458, 1432, 1271, 1150 | 0.98(9H, s), 3.15(2H, dd), 3.56(2H, dd), 3.90(2H, s), 4.82(2H, s), 7.32(1H, d), 7.68 (1H, dd), 8.32(1H, d) |
| 139 | 1662, 1550, 1459, 1431, 1263, 1145 | 0.31(2H, m), 0.58(2H, m), 1.24(1H, m), 3.16(2H, t), 3.56(2H, t), 4.00(2H, t), 4.83(2H, s), 7.32(1H, d), 7.64(1H, bd), 8.32(1H, bs) |
| 140 | 1666, 1550, 1458, 1446, 1265, 1146 | 2.68(1H, m), 2.84(1H, m), 3.18(2H, dd), 3.30(2H, dd), 3.56(2H, dd), 4.10(1H, m), 4.38(1H, m), 4.80(2H, s), 7.33(1H, d), 7.66(1H, dd), 8.32(1H, d) |
| 141 | 1664, 1548, 1459, 1418,, 1268, 1143 | 1.61(1H, m), 1.78'(1H, m), 2.19(2H, m), 2.39(2H, m), 3.15(2H, t), 3.56(2H, t), 4.82(2H, s), 5.02(1H, m), 7.32(1H, d), 7.64(1H, bd), 8.32(1H, bs) |
| 142 | 1662, 1542, 1507, 1458, 1419, 1233 | 3.17(2H, t), 3.60(2H, t), 4.77(2H, m), 4.82(2H, s), 4.91(2H, m), 5.46(1H, tt), 7.34(1H, d), 7.65(1H, dd), 8.33(1H, d) |
| 143 | 1650, 1547, 1463, 1430, 1263, 1238 | 1.58(2H, m), 1.72-1.85(4H, m), 1.93(2H, m), 3.14(2H, t), 3.54(2H, t), 4.81(2H, s), 5.16(1H, m), 7.32(1H, d), 7.64(1H, dd), 8.32(1H, d) |
| 144 | 1665, 1550, 1462, 1420, 1212, 1058 | 1.68(1H, m), 2.06(1H, m), 2.69(1H, m), 3.17(2H, dd), 3.58(2H, dd), 3.63(1H, m), 3.75(1H, m), 3.87(2H, m), 4.09(1H, m), 4.16(1H, m), 4.81(2H, s), 7.33(1H, d), 7.64(1H, dd), 8.32(1H, d) |

TABLE 20-continued

| | | |
|---|---|---|
| 145 | 1665, 1552, 1460, 1444, 1238, 1151 | 1.35(3H, s), 1.42(3H, s), 3.18(2H, dd), 3.62(2H, dd), 3.79(1H, m), 4.10(1H, m), 4.20(2H, d), 4.40(1H, m), 4.81(2H, s), 733(1H, d), 7.64(1H, bd), 8.31(1H, bs) |
| 146 | 1660, 1546, 1458, 1264, 1237, 1150 | 1.78(2H, m), 1.99(2H, m), 3.16(2H, t), 3.52(2H, m), 3.57(2H, t), 3.99(2H, m), 4.82(2H, s), 4.89(1H, m), 7.32(1H, d), 7.64(1H, dd), 8.32(1H, d) |
| 147 | 1661, 1543, 1423, 1236, 1144, 1054 | 1.25-1.65(5H.m), 1.85(1H, m), 3.15(2H, t), 3.45(1H, m), 3.54(2H, t), 3.65(1H, m), 3.99(1H, m), 4.12(2H, d), 4.82(2H, s), 7.32(1H, d), 7.65(1H, dd), 8.30(1H, d) |
| 148 | 1698, 1522, 1349, 1198, 1143, 1110 | 3.29(2H, t), 3.78(2H, t), 4.79(2H, s), 7.41(2H, d), 7.47(1H, dd), 8.25(2H, d), 8.35(1H, d) |
| 149 | 1654, 1550, 1444, 1421, 1291, 1154 | 3.15(2H, dd), 3.54(2H, dd), 3.82(3H, s), 4.80(2H, s), 5.27(2H, s), 6.86(1H, d), 6.93(1H, m), 7.27(1H, m), 7.30(1H, d), 7.39(1H, d), 7.63(1H, dd), 8.29(1H, d) |
| 150 | 1654, 1544, 1459, 1439, 1287, 1131 | 3.18(2H, t), 3.58(2H, t), 4.80(2H, s), 5.22(2H, s), 7.27(1H, m), 7.32(1H, d), 7.62(1H, dd), 7.78(1H, m), 8.31(1H, d), 8.56(1H, m), 8.69(1H, s) |

TABLE 21

| | | |
|---|---|---|
| 151 | | 3.18(2H, t), 3.52(2H, t), 4.59(2H, s), 5.22(2H, s), 7.30(1H, d), 7.45(2H, dd), 8.32(1H, d), 8.64(2H, dd) |
| 152 | 1669, 1558, 1457, 1420, 1260, 1039 | 3.16(2H, dd), 3.56(2H, dd), 4.79(2H, s), 5.15(2H, s), 6.34(1H, dd), 6.44(1H, d), 7.31(1H, d), 7.40(1H, d), 7.63(1H, dd), 8.29(1H, d) |
| 153 | 1657, 1557, 1457, 1428, 1240, 1146 | 3.16(2H, t), 3.57(2H, t), 4.79(2H, s), 5.01(2H, s), 6.50(1H, s), 7.31(1H, d), 7.38(1H, d), 7.52(1H, bs), 7.62(1H dd), 8.30(1H, d) |
| 154 | 1660, 1551, 1458, 1440, 1237, 1146 | 3.15(2H, t), 3.55(2H, t), 4.77(2H, s), 5.34(2H, s), 6.96(1H, t), 7.13-7.30(3H, overlap), 7.62(1H, dd), 8.28(1H, d) |
| 155 | 1650, 1546, 1460, 1440, 1263, 1146 | 3.16(2H, t), 3.57(2H, t), 4.79(2H, s), 5.20(2H, s), 7.16(1H, d), 7.27-7.32(3H, overlap), 7.62(1H, dd), 8.30(1H, d) |
| 156 | 1682, 1548, 1461, 1418, 1240, 1104 | 3.22(2H, dd), 3.67(2H, dd), 4.84(2H, s), 7.30-7.34(1H, m), 7.36(1H, d), 7.57(1H, m), 7.67(1H, dd), 8.34(1H, d), 8.46(1H, m), 8.53(1H, m) |
| 158 | 1667, 1547, 1528. 1443, 1256, 1128 | 3.19(2H, t), 3.65(2H, t), 3.81(3H, s), 4.85(2H, s), 7.46(1H, s) |
| 159 | 1664, 1552, 1529, 1432, 1237, 1192 | 1.36(3H, t), 3.18(2H, t), 3.63(2H, t), 4.24(2H, q), 4.86(2H, s), 7.46(1H, s) |
| 160 | 1667, 1550, 1530, 1418, 1250, 1048 | 1.33(6H, d), 3.16(2H, t), 3.62(2H, t), 4.87(2H, s), 5.03(1H, s), 7.45(1H, s) |
| 161 | 1661, 1550, 1528, 1446, 1238, 1186 | 0.95(3H, t), 1.44(2H, m), 1.72(2H, m), 3.18(2H, t), 3.64(2H, t), 4.19(2H, q), 4.86(2H, s), 7.46(1H, s) |
| 162 | 1661, 1549, 1527, 1429, 1252, 1052 | 1.70(1H, m), 2.07(1H, m), 2.71(1H, m), 3.18(2H, dd), 3.65(2H, dd), 3.78(1H, m), 3.88(2H, m), 4.11(1H, m), 4.17(1H, m), 4.86(2H, s)7.45(1H, s) |
| 163 | 1680, 1550, 1528, 1412, 1248, 1183 | 3.19(2H, dd), 3.68(2H, dd), 4.89(2H, s), 7.21(3H, overlap), 7.37(2H, m), 7.47(1H, s) |
| 167 | 1671, 1587, 1495, 1460, 1252, 1081 | 1.31(6H, d), 2.05(2H, m), 3.10(2H, t), 3.32(2H, m), 4.69(2H, s), 4.94(1H, sep), 7.31(1H, d), 7.63(1H, dd), 8.30(1H, d) |
| 168 | 1667, 1566, 1498, 1461, 1391, 1183 | 2.14(2H, m), 3.22(2H, m), 3.53(2H, m), 4.74(2H, s), 7.35(1H, d), 7.72(1H, d), 8.36(1H, d) |
| 169 | 3370, 1730, 1648, 1599, 1460, 1138 | 3.35(2H, dd), 3.64(2H, dd), 3.71(3H, s), 4.55(2H, s), 7.31(1H, d), 7.65(1H, dd), 7.94(1H, bs), 8.29(1H, d) |

TABLE 22

| | | |
|---|---|---|
| 170 | 1655, 1522, 1459, 1389, 1294, 1081 | 2.92(3H, s), 3.34(2H, dd), 3.55(2H, dd), 3.70(3H, s), 4.54(2H, s), 7.31(1H, d), 7.70(1H, dd), 8.28(1H, d) |
| 171 | 1658, 1550, 1421, 1265, 1240, 1144 | 3.07(2H, m), 3.58(2H, m), 4.59(2H, s), 7.18-7.58(5H, m), 7.70(1H, m), 7.78(1H, m), 8.36(1H, bs) |
| 172 | 2904, 1663, 1459, 1352, 1239, 1064 | 3.16(2H, dd), 3.57(2H, dd), 3.63-3.90(23H, m), 4.24(2H, d), 4.80(2H, s), 7.32(1H, d), 7.40(1H, dd), 7.65(1H, dd), 8.31(1H, d) |
| 173 | 1659, 1543, 1459, 1415, 1261, 1146 | 2.49(2H, m), 3.16(2H, t), 3.56(2H, t), 4.22(2H, t), 4.80(2H, s), 5.14(2H, m), 5.84(1H, m), 7.32(1H, d), 7.64(1H, dd), 8.31(1H, d) |

Production Example 1

3-(2-Chloro-5-pyridinylmethyl)-2-(benzoylimino)-thiazolidine ("Table 2", Compound No. 6)

3-(2-Chloro-5-pyridinylmethyl)-2-iminothiazolidine (227 mg, 1.1 mmol) and triethylamine (110 mg, 1.1 mmol) were dissolved in 10 ml of acetonitrile, into which, benzoyl chloride (141 mg, 1.0 mmol) dissolved in acetonitrile 5 ml was added under cooling with ice, and stirred at room temperature overnight. After distilling the solvent off under reduced pressure followed by extraction with ethyl acetate, the ethyl acetate layer was washed with 2N-hydrochloric acid, saturated aqueous sodium bicarbonate, and water in this order, and the ethyl acetate layer was dehydrated and dried, and then the ethyl acetate layer was distilled off, and remaining oil was purified by a silica gel column chromatography to obtain the intended substance. The crude crystal of the intended substance was washed with hexane. Yield: 160 mg (65%). Melting point: 133° C.

Production Example 2

3-(2-Chloro-5-pyridinylmethyl)-2-(phenylacetylamino)-thiazolidine ("Table 2", Compound No. 10)

To a solution of 3-(2-Chloro-5-pyridinylmethyl)-2-iminothiazolidine (132 mg, 0.5 mmol) and 1-ethyl-3-(3-dimethylaminopropyl)carbodiimide hydrochloride (96 mg, 0.5 mmol) and 4-dimethylaminopyridine (65 mg, 0.54 mmol) in 3 ml of dichloromethane, phenylacetic acid (68 mg, 0.5 mmol) was added in portions, and stirred at room temperature overnight. After distilling the solvent off, the resultant crude crystal was washed with 1% hydrochloric acid, recrystallized from ethyl acetate thereby obtaining the intended substance. Yield: 100 mg (58%). Melting point: 157-158° C.

Production Example 3

3-(2-Chloro-5-thiazolylmethyl)-2-(benzoylimino)-thiazolidine ("Table 4", Compound No. 57)

3-(2-Chloro-5-thiazolylmethyl)-2-iminothiazolidine (233 mg, 1.0 mmol) and sodium carbonate (120 mg, 1.1 mmol) were dissolved in 10 ml of water, into which, benzoyl chloride (141 mg, 1.0 mmol) dissolved in 5 ml of chloroform was added under cooling with ice, and thereafter stirred at room temperature for 2 hours. The chloroform layer was washed successively with 1% hydrochloric acid and water, dehydrated and dried, chloroform was distilled off, and remaining oil was purified by a silica gel column chromatography to obtain the intended substance. The crude crystal of the intended substance was recrystallized from ethyl acetate. Yield: 101 mg (30%). Melting point: 120° C.

Production Example 5

[[3-(2-Chloro-5-pyridinylmethyl)]-2-(3H)-thiazolidinilidene]urea ("Table 3", Compound No. 28)

3-(2-Chloro-5-pyridinylmethyl)-2-iminothiazolidine (227 mg, 1.1 mmol) and trimethyl isocyanate (110 mg, 1.1 mmol) were dissolved in 20 ml of acetonitrile, into which, several drops of triethylamine were added, and heated under reflux for 9 hours with stirring. After distilling the solvent off, the residue was combined with 5 ml of 2N hydrochloric acid, and allowed to stand overnight. The precipitating intended substance was recovered by filtration, and recrystallized from ethyl acetate. Yield: 104 mg (39%). Melting point: 158-159° C.

Production Example 6

3-(2-Chloro-5-pyridinylmethyl)-2-(methoxycarbonylimino)-thiazolidine ("Table 3", Compound No. 42)

3-(2-Chloro-5-pyridinylmethyl)-2-iminothiazolidine (227 mg, 1.1 mmol) and methyl chloroformate (165 mg, 1.2 mmol) were dissolved in 20 ml of acetonitrile, into which, potassium carbonate (114 mg, 1 mmol) was added in portions and stirred at room temperature overnight. The reaction solution was made free of solids, and the solids were washed with ethyl acetate, and from the wash the solvent was distilled off, and the resultant intended substance was recrystallized from ethyl acetate. Yield: 120 mg (42%). Melting point: 128-130° C.

Production Example 7

3-(2-Chloro-5-pyridinylmethyl)-2-(formylimino)-thiazolidine ("Table 4", Compound No. 58)

A mixture of 3-(2-Chloro-5-pyridinylmethyl)-2-iminothiazolidine (227 mg, 1.1 mmol) and 10 ml of ethyl formate was heated at the boiling point of ethyl formate for 5 hours with stirring. After distilling the excessive ethyl formate off followed by purification by a silica gel column chromatography, the resultant intended solid was washed with diethyl ether. Yield: 32 mg (13%). Melting point: 99-100° C.

Formulation Example 1

1. Powder Formulation

3 Parts by weight of the imino derivative of Compound No. 1 (Table 1), 40 parts by weight of a clay, 57 parts by weight of a talc were ground respectively and mixed to obtain a powder formulation.

Formulation Example 2

2. Wettable Powder

50 Parts by weight of the imino derivative of Compound No. 6 (Table 1), 5 parts by weight of lignin sulfonate, 3 parts by weight of an alkyl sulfonate, 42 parts by weight of a kieselguhr were ground respectively and mixed to obtain a wettable powder.

Formulation Example 3

3. Granule Formulation

5 Parts by weight of the imino derivative of Compound No. 21 (Table 3), 43 parts by weight of a bentonite, 45 parts by weight of a clay, 7 parts by weight of lignin sulfonate were mixed uniformly, combined with water and kneaded, and then subjected to an extruding granulator to fabricate into granules, which was dried to obtain a granule formulation.

Formulation Example 4

4. Emulsifiable Concentrate

20 Parts by weight of the imino derivative of Compound No. 71 (Table 5), 10 parts by weight of a polyoxyethylene alkylallyl ether, 3 parts by weight of a polyoxyethylene sorbitan monolaurate, 67 parts by weight of a xylene were mixed uniformly while dissolving to obtain an emulsifiable concentrate.

Experimental Example 1

1. Cotton Aphid Controlling Effect

The insecticides formulated in Production Examples were used under a practical condition to validate the pest controlling effects.

A cucumber cotyledon was dipped in a 100 μg/ml treatment solution obtained by a 5000-fold dilution with water of the wettable powder prepared in accordance with Formulation Example 2. This cotyledon was placed on a moistened filter paper placed on the bottom of a petri dish of 9 cm in diameter. On this treated leaf, 30 apterous viviparous female insects of the cotton aphid were allowed to inhabit, and then the petri dish was covered with the stopper, which was allowed to stand in a room whose temperature was constant at 25° C. After 120 hours, the number of viable insects was counted.

As a result, Compound Nos. 5, 9, 14, 21, 42, 43, 44, 45, 58, 61, 64, 65, 72, 73, 76, 78, 81, 90, 92, 103, 106, 113, 114, 115, 116, 118, 119, 122, 126, 128, 129, 130, 132, 135, 136, 139, 142, 144, and 146, as in the form of a wettable powder prepared in accordance with Formulation Example 2 at an active ingredient concentration of 100 μg/ml exhibited an effect as excellent as a lethality of 50% or higher.

Experimental Example 2

2. Green Peach Aphid Controlling Effect

On a 2-leaf stage Chinese cabbage seedling, 30 adult insects of green peach aphid were allowed to inhabit, and immobilized by allowing to stand for several days. Thereafter, the overground part was cut off, was dipped in a 100 μg/ml treatment solution obtained by a 5000-fold dilution with water of the wettable powder prepared in accordance with Formulation Example 2. This was placed on a moistened filter paper placed on the bottom of a petri dish of 9 cm in diameter, which was allowed to stand in a room whose temperature was constant at 25° C. After 120 hours, the number of viable insects was counted.

As a result, Compound Nos. 5, 6, 7, 9, 10, 11, 13, 14, 16, 18, 20, 21, 24, 29, 36, 37, 43, 44, 45, 64, 65, 72, 73, 76, 78, 90, 92, 103, 106, 113, 114, 115, 116, 118, 119, 122, 126, 128, 129, 130, 135, 136, 139, 142, 144, 146, and 160, as in the form of a wettable powder prepared in accordance with Formulation Example 2 at an active ingredient concentration of 100 μg/ml, exhibited an effect as excellent as a lethality of 80% or higher.

Experimental Example 3

3. Greenhouse Whitefly Controlling Effect

The overground part of the 1-leaf stage cucumber was dipped in a 100 μg/ml treatment solution obtained by a 5000-fold dilution with water of the wettable powder prepared in accordance with Formulation Example 2, and air-dried, and then transferred to a plastic container having a stopper. This was allowed to be inhabited with 20 adult insects of the greenhouse whitefly, covered with the stopper, and allowed to stand in a room whose temperature was constant at 25° C. After 120 hours, the number of viable insects was counted.

As a result, Compound Nos. 5, 6, 7, 9, 10, 11, 12, 13, 16, 17, 18, 20, 24, 29, 37, 43, 44, 45, 57, 64, 72, 73, 76, 78, 92, 113, 114, 115, 116, 118, 119, 122, 126, 128, 129, 130, 135, 136, 139, 144, and 146, as in the form of a wettable powder prepared in accordance with Formulation Example 2 at an active ingredient concentration of 100 μg/ml exhibited an effect as excellent as a lethality of 50% or higher.

Experimental Example 4

4. Two-Spotted Spider Mite Controlling Effect

A kidney bean leaf was allowed to be inhabited with 10 adult insects of two-spotted spider mite, and then dipped in a 100 μg/ml treatment solution obtained by a 5000-fold dilution with water of the wettable powder prepared in accordance with Formulation Example 2. After air drying, the cut end was wrapped with a cotton wet with water thereby supplying water to the common bean leaf. After 120 hours of allowing to stand in a room whose temperature was constant at 25° C., the number of viable insects was counted.

As a result, Compound Nos. 5, 6, 7, 9, 10, 11, 17, 24, 82, 90, 91, 107, 113, 135, 142, 171, and 173, as in the form of a wettable powder prepared in accordance with Formulation Example 2 at an active ingredient concentration of 100 μg/ml exhibited an effect as excellent as a lethality of 50% or higher.

In the above-indicated Experimental Examples 1 to 4, especially, Compound Nos. 5, 43, 44, 45, 72, 73, 76, 78, 90, 92, 103, 106, 113, 114, 115, 118, 119, 122, 126, 128, 129, 130, 135, 136, 139, 142, 144, and 146 exhibited excellent pest controlling effects.

Comparative Example 1

5. Greenhouse Whitefly Controlling Effect

For the purpose of comparison with the insecticide according to the invention, the pest controlling effect of the compound represented by Formula (12) disclosed in the above-indicated Patent Literature (Japanese Unexamined Patent Application Publication No. 63-150275) was validated.

Formula (12)

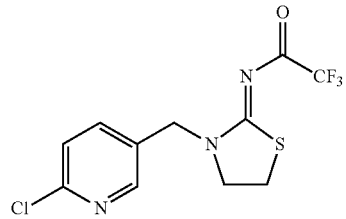

[C.23]

This compound was prepared into a wettable powder in accordance with Formulation Example 2. The overground part of the 1-leaf stage cucumber was dipped in a 100 μg/ml treatment solution obtained by a 5000-fold dilution with water of the prepared wettable powder, and air-dried, and then transferred to a plastic container having a stopper. This was allowed to be inhabited with 20 adult insects of the greenhouse whitefly, covered with the stopper, and allowed to stand in a room whose temperature was constant at 25° C. After 120 hours, the number of viable insects was counted.

As a result, at an active ingredient concentration of 100 μg/ml, the lethality was 25%. On the contrary, the insecticide according to the invention exhibited the lethality in the similar experiment (see Experimental Example 3) of 50% or higher at an active ingredient concentration of 100 μg/ml. Based on these findings, the insecticide according to the invention was revealed to have an excellent pest controlling effect.

INDUSTRIAL APPLICABILITY

A novel imino derivative according to the invention and an insecticide containing the same as an active ingredient exhibit an excellent controlling effect on agro-horticultural and household pests such as Hemiptera pests. Accordingly, the invention can widely be utilized in the fields of agro-horticultural production, livestock, and household sanitation, and can contribute a lot to such fields of the industry.

The invention claimed is:

1. An imino derivative represented by Formula (1):

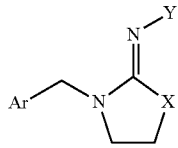

Formula (1)

wherein "Ar" denotes a heterocyclic group which may have a substituent on the ring; "X" denotes a sulfur atom or CH₂, NR; "R" denotes a hydrogen atom or an alkyl group;

when "Y" is COR₁, "R₁" denotes a hydrogen atom or a C1 to C5 alkyl group, a halogenated methyl except for a trifluoromethyl group, a C2 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C4)alkoxy(C1 to C5)alkyl group, a C1 to C3 alkoxy carbonyl group, a (C1 to C3)alkylsulfonyl(C1 to C3)alkyl group, a (C1 to C3)alkylthio(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a cyano(C1 to C3)alkyl group, a substituted or unsubstituted phenoxy(C1 to C3)alkyl group, a substituted or unsubstituted pyridylmethyl group, a substituted or unsubstituted imidazolylmethyl group, a furanyl group, a morpholino group, a norbornenyl group, an adamantyl group, an isothiocyanatomethyl group, or substituted or unsubstituted heterocyclic or aromatic ring;

when "Y" is CONR₃R₄, each of "R₃" and "R₄" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a C1 to C3 alkoxy group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group; "NR₃R₄" may form a ring; when "Y" is CONHCOR₅, "R₅" denotes a hydrogen atom or a C1 to C5 alkyl group, a C1 to C5 halogenated alkyl group, a C2 to C5 alkenyl group, a C2 to C5 halogenated alkenyl group, a substituted or unsubstituted C6 to C10 aryl group, a substituted or unsubstituted (C6 to C10)aryl(C1 to C3)alkyl group, a substituted or unsubstituted phenyl group;

when "Y" is CO₂R₉, "R₉" denotes a hydrogen atom or a C1 to C7 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a (C1 to C3)alkylthio (C1 to C3)alkyl group, a tri(C1 to C3 alkyl)silyl(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a substituted or unsubstituted phenyl group, a substituted or unsubstituted phenylmethyl group, a substituted or unsubstituted furanylmethyl group, a substituted or unsubstituted thienylmethyl group, a substituted or unsubstituted pyridylmethyl group, a succinimide group, a 18-crown-6-methyl group;

the abovementioned carbon chains may be substituted with halogen; and provided that, a compound wherein "Ar" denotes 2-chloro-5-pyridinyl, "X" denotes a sulfur atom, "Y" denotes CONH₂; a compound wherein "Ar" denotes pyridinyl, "X" denotes a sulfur atom, "Y" denotes 4-F-PhCO; and a compound wherein "Ar" denotes a heterocyclic group which may have a substituent on the ring, "X" denotes NR, "R" denotes a hydrogen atom or an alkyl group, "Y" denotes 4-(C1 to C4 halogenated alkyl)-3-pyridinylcarbonyl or 4-(C1 to C4 halogenated alkyl)-5-pyrimidinylcarbonyl are excluded.

2. The imino derivative according to claim 1 wherein "Ar" in Formula (1) is represented by Formula (13) or (14):

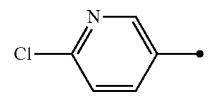

Formula (13)

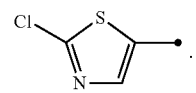

Formula (14)

3. A method for producing an imino derivative represented by Formula (1) shown above by reacting one compound selected from the group consisting of compounds (5) represented by Formula (5), anhydrides represented by Formula (6), and carboxylic acids represented by Formula (7) with a compound represented by Formula (4):

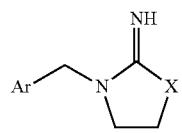

Formula (4)

wherein "Ar" denotes a heterocyclic group which may have a substituent on the ring; "X" denotes a sulfur atom or CH₂, NR; and "R" denotes a hydrogen atom or an alkyl group:

ACO—B                Formula (5)

ACOOCOA              Formula (6)

ACOOH                Formula (7)

wherein "B" denotes a halogen atom of Cl or Br, I, an OCOA group (a group formed by allowing each of an oxygen atom and a group A to form a single bond with a carbonyl group (CO)) or a hydroxyl group;

when "ACO" is COR₁, "R₁" denotes a hydrogen atom or a C1 to C5 alkyl group, a halogenated methyl except for a trifluoromethyl group, a C2 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C4)alkoxy(C1 to C5)alkyl group, a C1 to C3 alkoxy carbonyl group, a (C1 to C3)alkylsulfonyl(C1 to C3)alkyl group, a (C1 to C3)alkylthio(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a cyano(C1 to C3)alkyl group, a substituted or unsubstituted phenoxy(C1 to C3)alkyl group, a substituted or unsubstituted pyridylmethyl group, a substituted or unsubstituted imidazolylmethyl group, a furanyl group, a morpholino group, a norbornenyl group, an adamantyl group, an isothiocyanatomethyl group, or substituted or unsubstituted heterocyclic or aromatic ring;

when "ACO" is $CONR_3R_4$, each of "$R_3$" and "$R_4$" denotes a hydrogen atom or a C1 to C5 alkyl group, a C1 to C5 halogenated alkyl group, a C2 to C5 alkenyl group, a C2 to C5 halogenated alkenyl group, a C3 to C5 alkynyl group, a C1 to C3 alkoxy group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a C1 to C3 alkoxycarbonylmethyl group, a C3 to C7 substituted or unsubstituted cycloalkyl group, a 3-membered to 7-membered substituted or unsubstituted heterocycloalkyl group, a substituted or unsubstituted pyridylmethyl group, a substituted or unsubstituted benzenesulfonyl group; "$NR_3R_4$" may form a ring;

when "ACO" is $CO_2R_9$, "$R_9$" denotes a hydrogen atom or a C1 to C7 alkyl group, a C1 to C5 halogenated alkyl group, a C2 to C5 alkenyl group, a C2 to C5 halogenated alkenyl group, a C3 to C5 alkynyl group, a substituted or unsubstituted C6 to C10 aryl group, a substituted or unsubstituted (C6 to C10)aryl(C1 to C3)alkyl group, a (C1 to C3)alkoxy(C1 to C3)alkyl group, a (C1 to C3)alkylthio(C1 to C3)alkyl group, a tri(C1 to C3 alkyl)silyl(C1 to C3)alkyl group, a C3 to C7 substituted or unsubstituted cycloalkyl group, a 3-membered to 7-membered substituted or unsubstituted heterocycloalkyl group, a 3-membered to 7-membered substituted or unsubstituted heterocycloalkylmethyl group, a substituted or unsubstituted phenyl group, a substituted or unsubstituted phenylmethyl group, a substituted or unsubstituted furanylmethyl group, a substituted or unsubstituted thienylmethyl group, a substituted or unsubstituted pyridylmethyl group, a succinimide group, a 18-crown-6-methyl group;

the abovementioned carbon chains may be substituted with halogen; and provided that, a compound wherein "Ar" denotes 2-chloro-5-pyridinyl, "X" denotes a sulfur atom, "Y" denotes $CONH_2$; a compound wherein "Ar" denotes pyridinyl, "X" denotes a sulfur atom, "Y" denotes 4-F-PhCO; and a compound wherein "Ar" denotes a heterocyclic ring which may have a substituent on the ring, "X" denotes NR, "R" denotes a hydrogen atom or an alkyl group, "Y" denotes 4-(C1 to C4 halogenated alkyl)-3-pyridinylcarbonyl or 4-(C1 to C4 halogenated alkyl)-5-pyrimidinyl carbonyl are excluded.

4. An insecticide containing as an active ingredient an imino derivative according to claim 1.

* * * * *

UNITED STATES PATENT AND TRADEMARK OFFICE
CERTIFICATE OF CORRECTION

PATENT NO. : 8,309,733 B2
APPLICATION NO. : 13/001843
DATED : November 13, 2012
INVENTOR(S) : S. Kagabu et al.

It is certified that error appears in the above-identified patent and that said Letters Patent is hereby corrected as shown below:

On the Title Page item (73) Assignees, "Meji Seika Pharma Co., Ltd." should be
-- Meiji Seika Pharma Co., Ltd. --.

Signed and Sealed this
Twelfth Day of March, 2013

Teresa Stanek Rea
*Acting Director of the United States Patent and Trademark Office*